(12) United States Patent
Leibovici

(10) Patent No.: US 10,675,417 B2
(45) Date of Patent: Jun. 9, 2020

(54) METHOD AND APPARATUS FOR APPLYING AN ANESTHETIC AND BACTERICIDE

(71) Applicant: Leibovici LLC, Wellington, FL (US)

(72) Inventor: Jacob Leibovici, Wellington, FL (US)

(73) Assignee: Leibovici, LLC, Wellington, FL (US)

( * ) Notice: Subject to any disclaimer, the term of this patent is extended or adjusted under 35 U.S.C. 154(b) by 164 days.

(21) Appl. No.: 16/017,379

(22) Filed: Jun. 25, 2018

(65) Prior Publication Data

US 2018/0369504 A1 Dec. 27, 2018

Related U.S. Application Data

(63) Continuation-in-part of application No. 15/094,754, filed on Apr. 8, 2016, now Pat. No. 10,004,855, which is a continuation-in-part of application No. 14/453,475, filed on Aug. 6, 2014, now Pat. No. 9,656,028, which is a continuation-in-part of application No. 13/927,454, filed on Jun. 26, 2013, now Pat. No. 9,561,334, which is a continuation-in-part of application No. 12/557,753, (Continued)

(51) Int. Cl.
| | |
|---|---|
| A61M 5/32 | (2006.01) |
| A61M 5/42 | (2006.01) |
| A61M 5/31 | (2006.01) |
| A61C 19/08 | (2006.01) |
| A61M 19/00 | (2006.01) |
| A61M 5/20 | (2006.01) |
| A61M 5/24 | (2006.01) |
| A61M 5/00 | (2006.01) |

(52) U.S. Cl.
CPC ............ *A61M 5/422* (2013.01); *A61C 19/08* (2013.01); *A61M 5/3129* (2013.01); *A61C 2203/00* (2013.01); *A61M 5/008* (2013.01); *A61M 5/20* (2013.01); *A61M 5/24* (2013.01); *A61M 5/3148* (2013.01); *A61M 19/00* (2013.01); *A61M 2005/2414* (2013.01); *A61M 2202/048* (2013.01)

(58) Field of Classification Search
CPC .. A61M 2005/1787; A61M 2005/2414; A61M 2205/3606; A61M 5/19; A61M 5/24; A61M 5/422
See application file for complete search history.

(56) References Cited

U.S. PATENT DOCUMENTS

| | | | | |
|---|---|---|---|---|
| 4,725,265 A | * | 2/1988 | Sairenji ................. | A61M 5/422 604/112 |
| 2009/0326478 A1 | * | 12/2009 | Salzman ............. | A61M 5/3129 604/207 |
| 2011/0098634 A1 | * | 4/2011 | Wycoki ................. | A61M 5/158 604/22 |

* cited by examiner

*Primary Examiner* — Rebecca E Eisenberg
(74) *Attorney, Agent, or Firm* — McHale & Slavin, P.A.

(57) ABSTRACT

A method and an apparatus for applying an anesthetic includes a receptacle having an upper end, a substantially hollow interior, a lower end having a tube or nozzle extending therefrom, and an attachment for attaching to the barrel of a syringe or vice versa. The receptacle receives a container or canister containing an endothermic gas or vapor (propellant) that rapidly absorbs heat when released to the atmosphere. A depressible actuating member or trigger propels the gas or vapor through an outlet nozzle that is oriented to project a stream of gas or vapor along a delivery axis that intersects a delivery axis of the needle, therefore, the gas or vapor can be successively delivered to an injection site with minimal repositioning of the housing.

23 Claims, 47 Drawing Sheets

Related U.S. Application Data filed on Sep. 11, 2009, now Pat. No. 8,500,678, which is a continuation-in-part of application No. 11/636,859, filed on Dec. 11, 2006, now abandoned.

(60) Provisional application No. 62/145,322, filed on Apr. 9, 2015, provisional application No. 60/733,757, filed on Mar. 7, 2006.

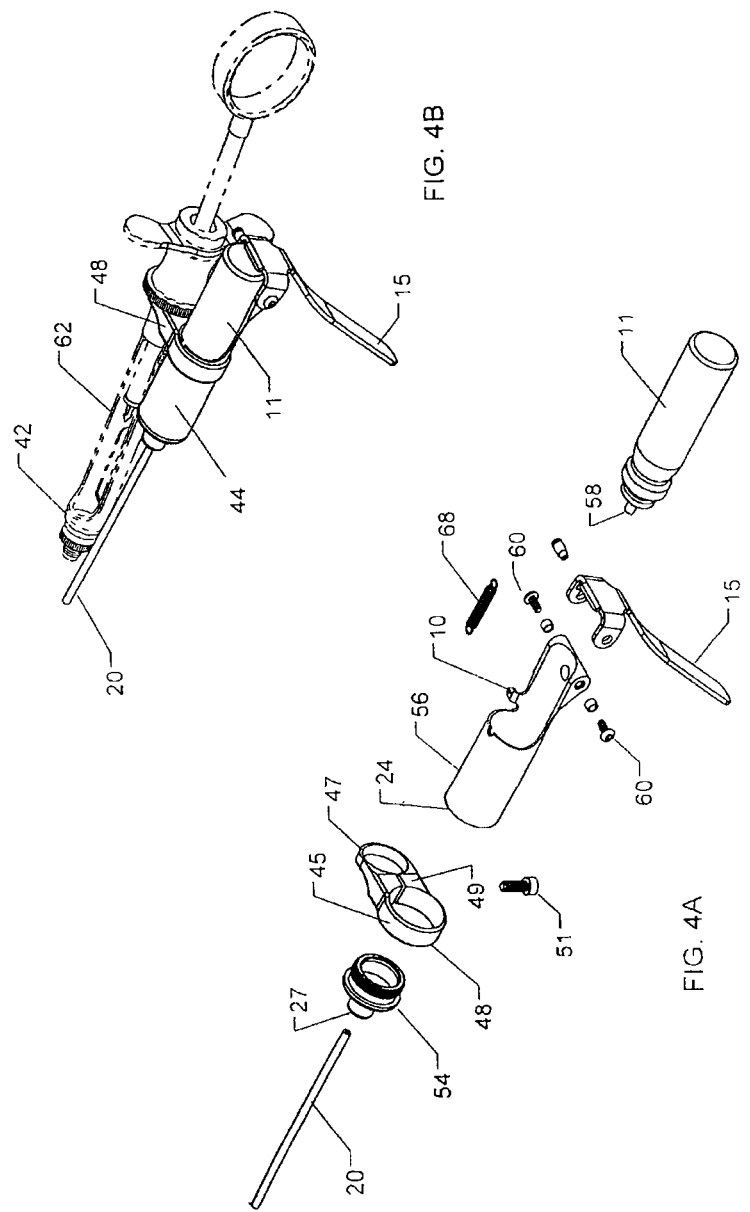

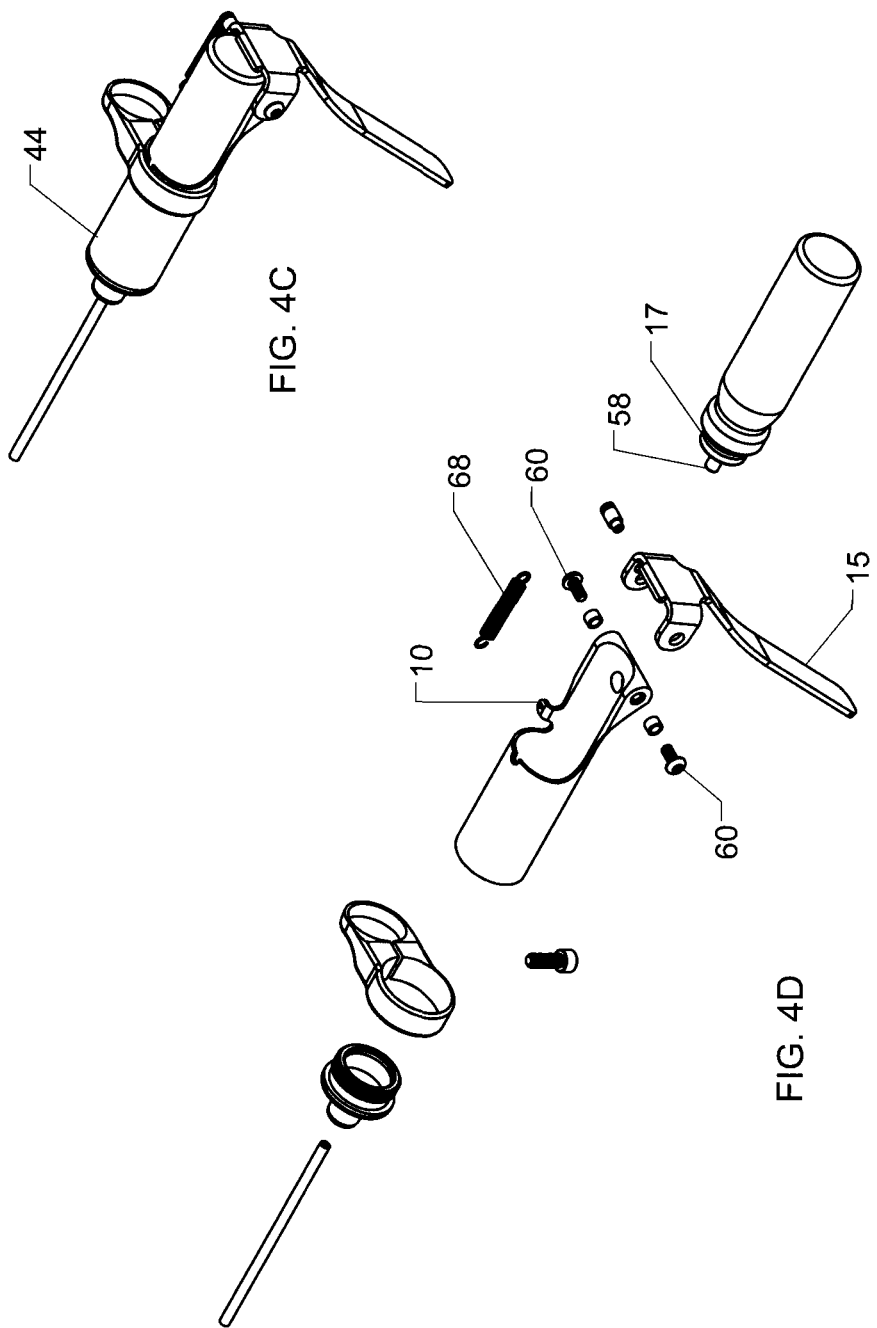

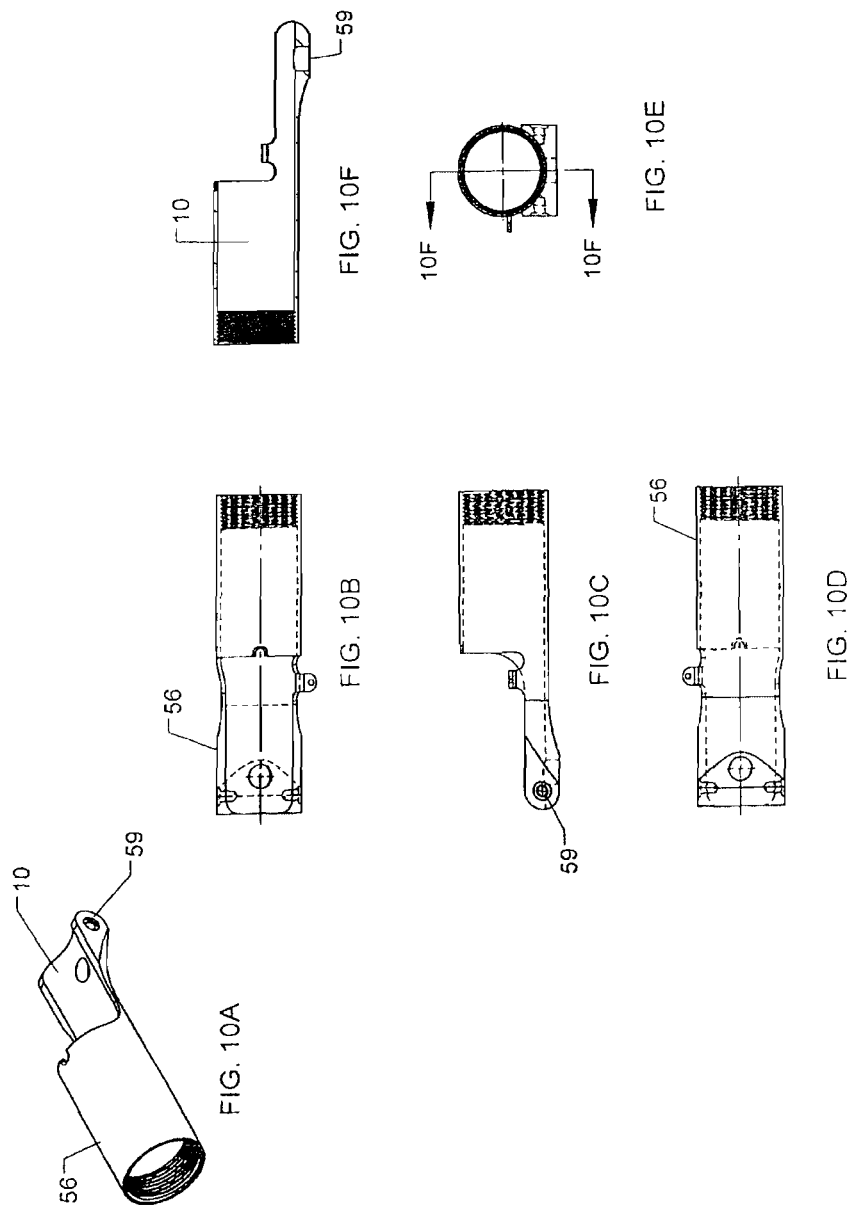

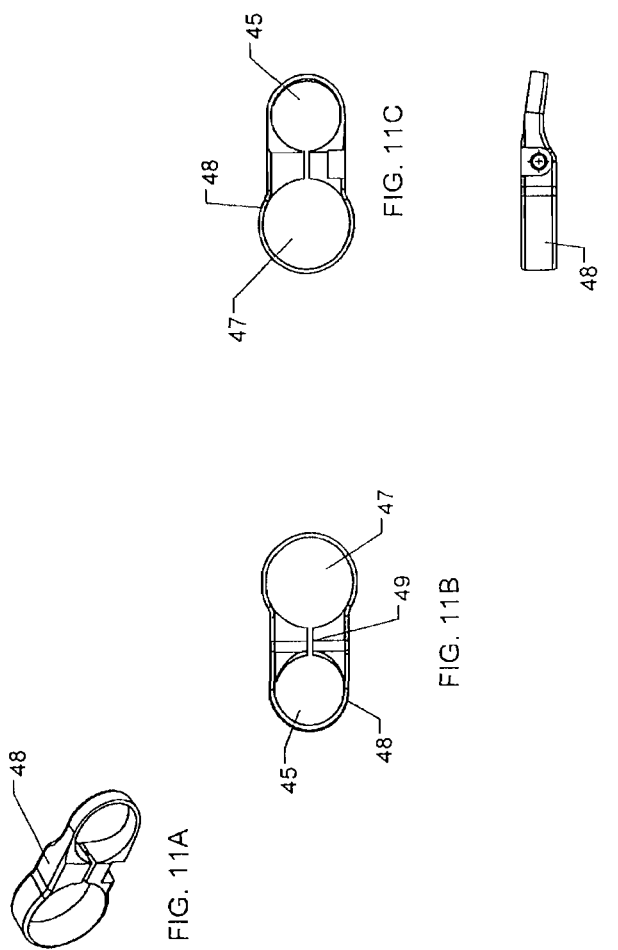

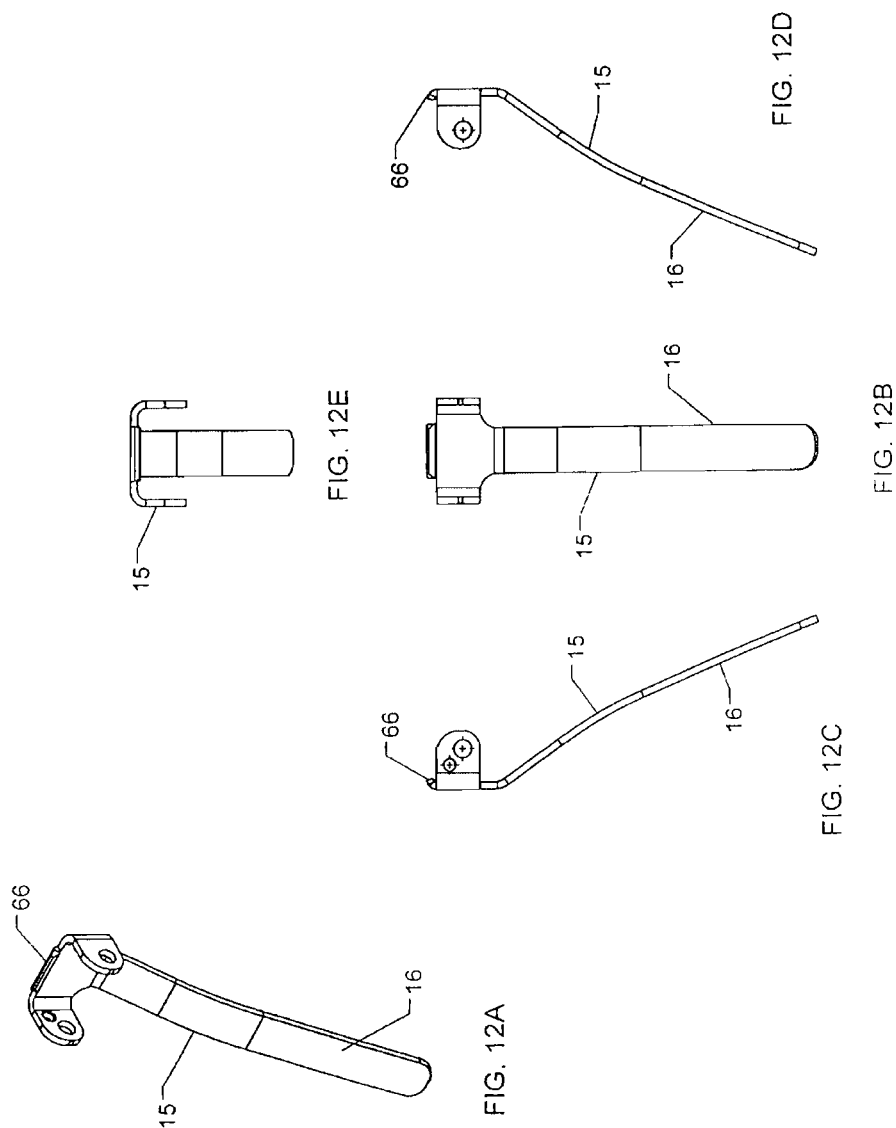

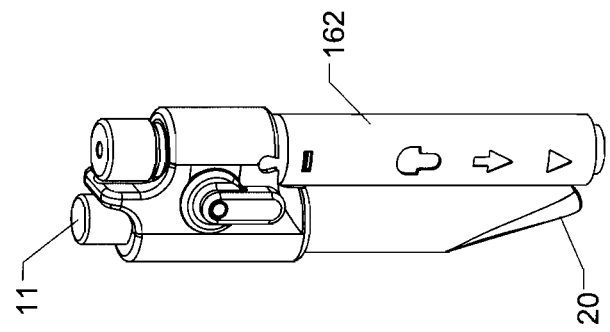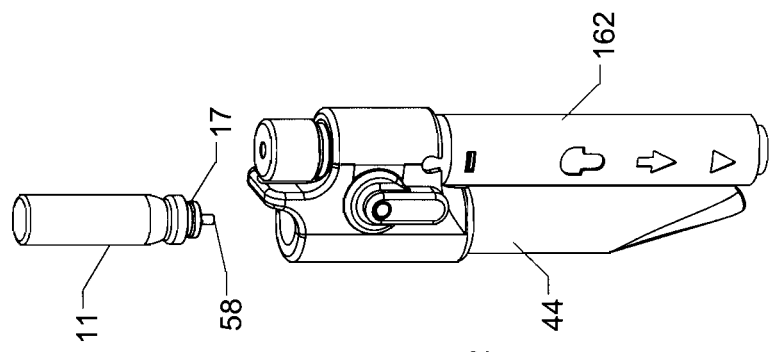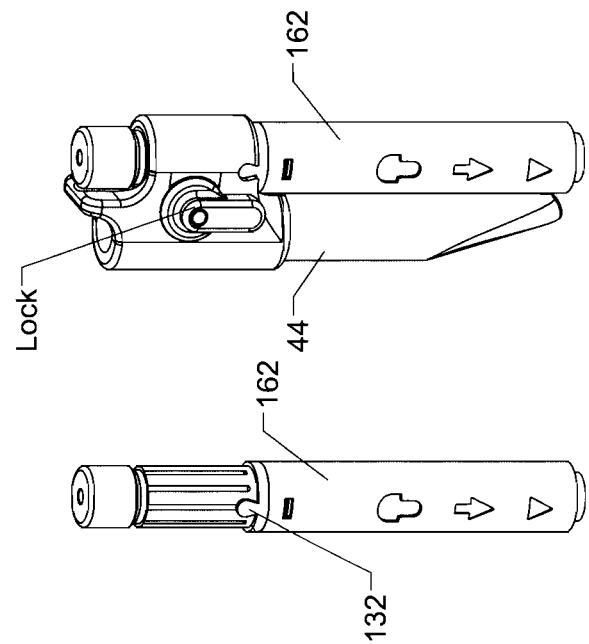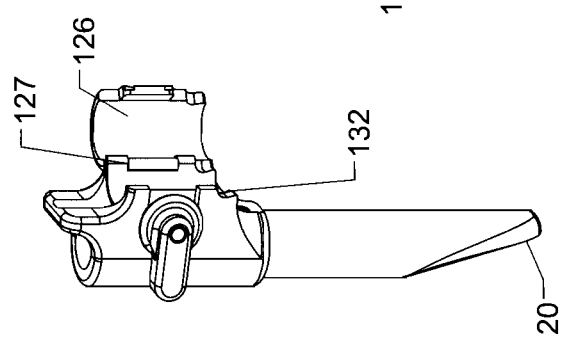

METHOD AND APPARATUS FOR APPLYING AN ANESTHETIC AND BACTERICIDE

PRIORITY CLAIM

In accordance with 37 C.F.R. 1.76, a claim of priority is included in an Application Data Sheet filed concurrently herewith. Accordingly, the present invention claims priority as a continuation-in-part of U.S. patent application Ser. No. 15/094,754, entitled "METHOD AND APPARATUS FOR APPLYING AN ANESTHETIC AND BACTERICIDE", filed Apr. 8, 2016, which claims priority to U.S. Provisional Patent Application No. 62/145,322, entitled "METHOD AND APPARATUS FOR APPLYING AN ANESTHETIC AND BACTERICIDE", filed Apr. 9, 2015, which claims priority as a continuation-in-part of U.S. patent application Ser. No. 14/453,475, entitled "METHOD AND APPARATUS FOR APPLYING AN ANESTHETIC AND BACTERICIDE", filed Aug. 6, 2014, which is a continuation-in-part of Ser. No. 13/927,454, entitled "METHOD AND APPARATUS FOR APPLYING AN ANESTHETIC AND BACTERICIDE", filed Jun. 26, 2013, which is a continuation-in-part of U.S. patent application Ser. No. 12/557,753, entitled "METHOD AND APPARATUS FOR APPLYING AN ANESTHETIC", filed Sep. 11, 2009, now U.S. Pat. No. 8,500,678, issued Aug. 6, 2013, which is a continuation-in-part of U.S. application Ser. No. 11/636,859, entitled "DENTAL SYRINGE", filed on Dec. 11, 2006, now abandoned, which claims the priority to U.S. Provisional Patent Application No. 60/733,757, entitled "CRYO-SYRINGE", filed on Mar. 7, 2006. The contents of which the above referenced applications are incorporated herein by reference.

FIELD OF THE INVENTION

Generally, the invention relates to an apparatus for applying an anesthetic to a patient. In particular, the apparatus comprises a receptacle for a liquefied endothermic gas and system for dispensing the endothermic gas which is removably attached to a syringe barrel.

BACKGROUND

Syringes are employed millions of times daily all over the world to inject medicines into people as well as animals. Many times, injections are made in areas of the body that are somewhat less sensitive to pain. Other locations of the body where injections are contemplated are significantly more sensitive to pain and the patient feels a pinching sensation that may be quite painful as the syringe needle is inserted beneath the skin. Such areas include, for example, gums, areas of the face such as the forehead, as well as the lips. To minimize the pain that results when the injection needle penetrates, for example, a patient's gums, the dental practitioner will often apply a topical agent to the injection site using a cotton swab. Because the deadening agent is only applied topically, it is not effective as it does not cross the skin/mucosal membranes and misleads the patient into a false expectation of a painless injection. As a result, injecting an anesthetic often causes significant pain at the injection site. In other cases, such as diabetics, patients may be required to self-medicate on a daily basis. The repeated injections often create sensitive areas where injections are painful to the patient. This pain may cause patients to delay or omit medication to avoid the pain associated therewith.

SUMMARY

There is currently a need for a means of minimizing the pain associated with an injection. The present invention addresses this need by providing a syringe having a liquid anesthetic, or a liquid anesthetic cartridge and a compressed gas or vapor canister therein, or a receptacle for receiving a gas or vapor canister, wherein the receptacle comprises a clip for attaching a syringe, e.g. piggyback. One chamber within the syringe or syringe cartridge includes a conventional anesthetic while the canister includes a compressed, endothermic gas or vapor that rapidly absorbs heat when released to the atmosphere; the endothermic gas or vapor is first applied to the injection site prior to the anesthetic injection to minimize the pain associated with conventional anesthesia techniques. Furthermore, the gas or vapor also blanches the mucosa (along with popping bubbles due to the boiling of the liquid phase), allowing a practitioner to readily identify the pretreated injection site so that the needle is not inserted into an unanesthetized area.

Embodiments of the invention are also directed to an apparatus comprising a syringe, a receptacle which is removably attached to the syringe barrel and which accommodates a canister comprising a gaseous (vaporous) anesthetizing composition. The receptacle further comprises an elongated nozzle or a short nozzle for attaching a tube. The apparatus comprises an actuating member which acts to dispense the contents of a container or canister containing the anesthetic composition. The actuating member comprises a lever and a spring biased means for the controlled release of the gaseous (vaporous) anesthetizing composition.

Embodiments of the invention are further directed to a gaseous anesthetizing canister assembly for attachment to a single use autoinjector type syringe. The anesthetizing canister assembly includes a collar that surrounds the autoinjector syringe for attachment. The canister assembly contains a high pressure canister filled with endothermic gas and a trigger mechanism for releasing the endothermic gas through a nozzle. The nozzle provides a predetermined spray pattern for directing the endothermic gas toward the skin to provide an anesthetized area. The autoinjector syringe can then be activated to insert the needle into the anesthetized area without pain to the user.

Other aspects are described infra.

BRIEF DESCRIPTION OF THE DRAWINGS

FIG. 4A is an exploded view of one embodiment of a module of the present invention;

FIG. 4B is a perspective view of the embodiment illustrated in FIG. 4A attached to a syringe;

FIG. 4C is a perspective view of the module of FIG. 4A;

FIG. 4D is an exploded view of the module of FIG. 4A;

FIG. 10A illustrates one embodiment of an adjunctive chamber suitable for use with the present device;

FIG. 10B is a front view of the adjunctive chamber illustrated in FIG. 10A;

FIG. 10C is a side view of the adjunctive chamber illustrated in FIG. 10A;

FIG. 10D is a rear view of the adjunctive chamber illustrated in FIG. 10A;

FIG. 10E is a top view of the adjunctive chamber illustrated in FIG. 10A;

FIG. 10F is a section view of the adjunctive chamber taken along lines 10F-10F of FIG. 10E;

FIG. 11A is a perspective view of one embodiment of the sleeve of the present invention;

FIG. 11B is a top view of the sleeve illustrated in FIG. 11A;

FIG. 11C is a bottom view of the sleeve illustrated in FIG. 11A with portions illustrated in phantom;

FIG. 11D is a front view of the sleeve illustrated in FIG. 11A;

FIG. 12A is a perspective view of one embodiment of the lever of the present invention;

FIG. 12B is a top view of the lever illustrated in FIG. 12A;

FIG. 12C is a left side view of the lever illustrated in FIG. 12A;

FIG. 12D is a right side view of the lever illustrated in FIG. 12A;

FIG. 12E is a top view of the lever illustrated in FIG. 12A;

FIG. 13A is a top isometric view of one embodiment of an autoinjector syringe suitable for use with the present invention;

FIG. 13B is a top isometric view of one embodiment of an adjunctive chamber suitable for use with an autoinjector syringe;

FIG. 14 is a top isometric view illustrating the adjunctive chamber secured to the autoinjector syringe of FIG. 13A;

FIG. 15 is a top isometric view illustrating insertion of a gas canister into the autoinjector syringe;

FIG. 16 is a top isometric view illustrating the fully assembled adjunctive chamber and autoinjector syringe;

DETAILED DESCRIPTION

Figure 2:
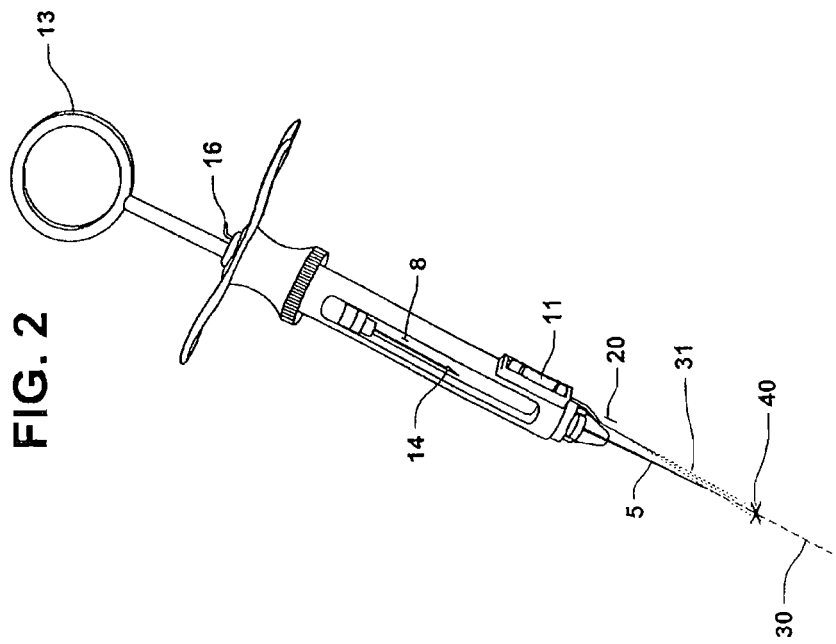
FIG. 2 is a plan view of the dental syringe with the cartridge and canister installed in their corresponding chambers.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

Referring to FIGS. 1-20, embodiments of the present invention relate to a method and apparatus of applying an anesthetic. In some embodiments, the apparatus comprises an elongated tubular housing 1 having an outer wall 2, an upper end 3, a substantially hollow interior, and a lower end 4 having an injection needle 5 extending therefrom. On the housing outer wall is an elongated opening 6 in communication with an anesthetic chamber 7 formed within the housing interior. The anesthetic chamber receives a cartridge 8 having a conventional dental anesthetic stored therein.

The outer wall also includes a smaller opening 9 that is in communication with an adjunctive chamber 10 for receiving a canister 11. The canister includes an endothermic gas (vapor) or "freeze spray" solution that rapidly absorbs heat when dispersed into the atmosphere.

Coaxially received within the anesthetic chamber 7 is a plunger 12 having a thumb ring 13 at an upper end and a spear 14 at a lower end; the spear penetrates a membrane on the upper end of the anesthetic cartridge 8 to force fluid therein into the injection needle 5.

Coaxially received within the adjunctive chamber 10 is a depressible trigger 15 having a handle 16 at an upper end that protrudes from the upper end of the housing. Depressing the trigger opens the valve assembly 17 of the canister 11, propelling the gaseous or vaporous solution contained within canister 11 through an outlet nozzle 20 on the lower end of the housing. The nozzle 20 is oriented to project a stream of gas or vapor along a delivery axis 31 that intersects a delivery axis 30 of the needle, preferably at a point 40 immediately adjacent to the needle outlet. Accordingly, a practitioner can first deaden a proposed injection site and then immediately insert the needle with little movement or repositioning of the syringe.

The method of applying an anesthetic using the syringe described above includes initially dispersing the heat-absorbing, endothermic gas or vapor from the canister 11 onto a proposed injection site by depressing the trigger 15. Because of its physical properties, the heat-absorbing substance constricts blood flow at the injection site, and temporary numbing occurs. The freeze spray stops the propagation of the painful nerve stimuli, and the patient feels the tactile or pressure as opposed to the pain sensation. The pressure nerve fibers supersede the painful nerve fibers so that the mechanical contraction of the muscles blocks the transmission of pain perception, according to the Gate theory. The use of the endothermic "freeze spray" also temporarily distracts the patient by creating a "popping" noise (due to the boiling of the liquid under pressure) that diverts the patient's attention away from any potential or anticipated pain. Finally, because the solution blanches the mucosa, a readily-visible target is created for insertion of the needle to assure that the deadened area is not bypassed. The aerosol propellants or gas (vapor) used as anesthetic herein avoid the drawbacks associated with traditional anesthetics. The gas or vapor freezes (blanches) the area of administration, allowing for the painless insertion of the needle to deliver the pharmaceutical drug, vaccine, BOTOX®, hair transplant and the like.

When the practitioner observes that the injection site mucosa has been blanched, the site is effectively deadened and a painless, concomitant injection is possible. The practitioner can then quickly inject the anesthetic into the blanched injection site by inserting the injection needle 5 and depressing the plunger 12. Because of the positioning of the gas or vapor outlet nozzle 20 and needle outlet 21, the dispersal of the gas or vapor and subsequent injection of anesthetic can be accomplished almost concurrently and with no pain to the patient.

Referring to FIGS. 3, 4A-D, 9A-C, 10A-F, 11A-D and 12A-E, alternative embodiments of the present invention are illustrated. In these embodiments, an apparatus comprising a module 44 is removably attached to a syringe barrel 62 and accommodates a canister 11 comprising a gaseous (vapor) anesthetizing composition. The module 44 includes an elongated outlet nozzle 20 for directing the gaseous (vapor) anesthetizing composition to intersect with the delivery axis 30 (FIG. 2) of the needle 5. The module includes an adjunct chamber frame 56, attachment means in the form of clips 23 or a sleeve 48, a trigger 15 and an outlet nozzle 20. The adjunct chamber frame 56 functions to contain the canister 11, as well as providing support for the trigger 15, clip(s) 23 and the dispenser cap 54. The trigger member 15 (FIG. 12A-E) functions to dispense the contents of the canister 11 containing the anesthetic composition by forcing the canister to slide within the adjunctive chamber 10 of the adjunct chamber frame 56. During the sliding action, the dispensing tube 58 of the canister 11 is pressed against the dispenser tube shoulder 55 to cause the canister valve 17 to open allowing compressed gas to escape through the dispenser tube 58. The trigger 15 is secured to the adjunct chamber frame 56 via pivot pins 60. The pivot pins 60 cooperate with pivot apertures 59 in the adjunct chamber frame 56. The pivot pins are positioned to allow the trigger to rotate thereabout so that the handle 16 can be utilized to force the ram 66 against the base of the canister 11 to cause the movement within the adjunctive chamber 10 to allow the pressurized gas to be released. A biasing means in the form of a spring 68 may be utilized to return the trigger to its original position. In some embodiments, the module 44 is disposable. In other embodiments, the syringe 42 is disposable. In yet other embodiments, the canister 11 is disposable. In other embodiments, any one or combination of parts of the apparatus is disposable.

Still referring to FIGS. 3, 4A-D, 9A-C, 10A-F, 11A-D and 12A-E, the module 44 includes an adjunctive chamber 10 for accepting a gas cartridge 8. The outer diameter of the module includes an attachment means which may comprise a clip 23 (FIG. 3) or sleeve 48 (FIG. 4A) which are adapted to cooperate with the outer diameter of a syringe barrel 62 for securing the module to the syringe. The clip 23 preferably includes a pair of arcuate members 24 made of a flexible resilient material so that the arcuate members may be temporarily enlarged by flexing to allow the arcuate members to snap over the outer diameter of the syringe barrel 62. In this manner, the module may be attached to syringe barrels of differing diameters to provide versatility to the device. The sleeve member 48 is also constructed from a flexible resilient material, such as plastic, and includes a slot 49 extending between two barrels 45, 47. In operation, the slot 49 may be expanded to allow the first and second barrels 45, 47 to be slipped over the outer diameter of the module 44 and the syringe 42. A fastener 51 may be provided to compress the slot 49 in the sleeve member 48 to prevent slippage of the assembly during use.

Figure 8:
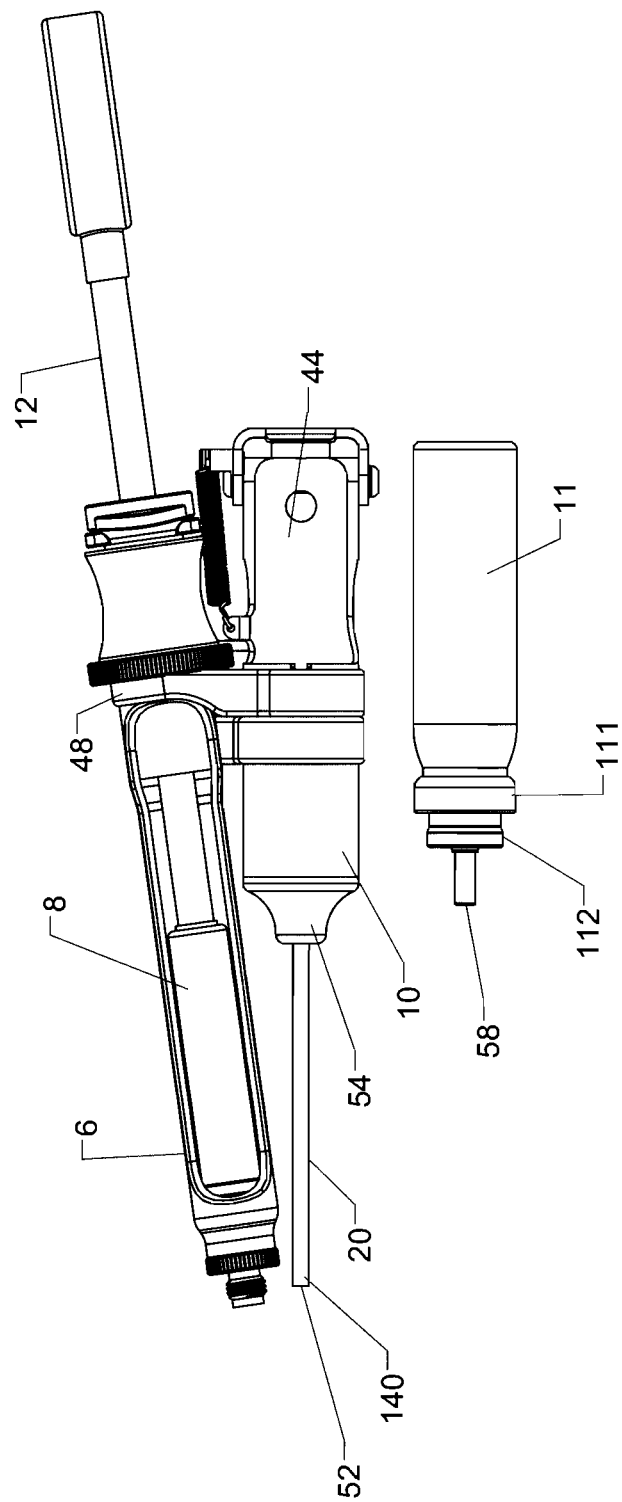
FIG. 8 is a partially exploded front view of the embodiment illustrated in FIG. 6.
Figure 9B:
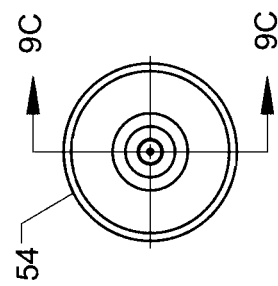
FIG. 9B is a front view of the dispenser cap illustrated in FIG. 9A.
Figure 9C:
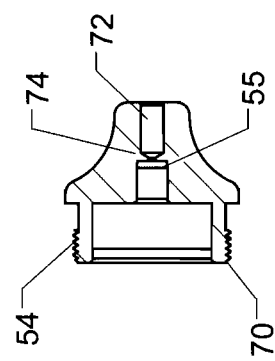
FIG. 9C is a section view taken along lines 9C-9C of FIG. 9B.
Figure 9A:
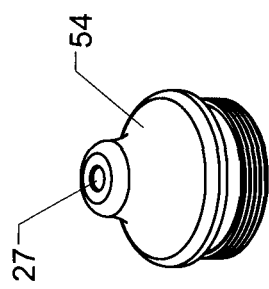
FIG. 9A is a perspective view of one embodiment of the dispenser cap of the present invention.
Figure 17:
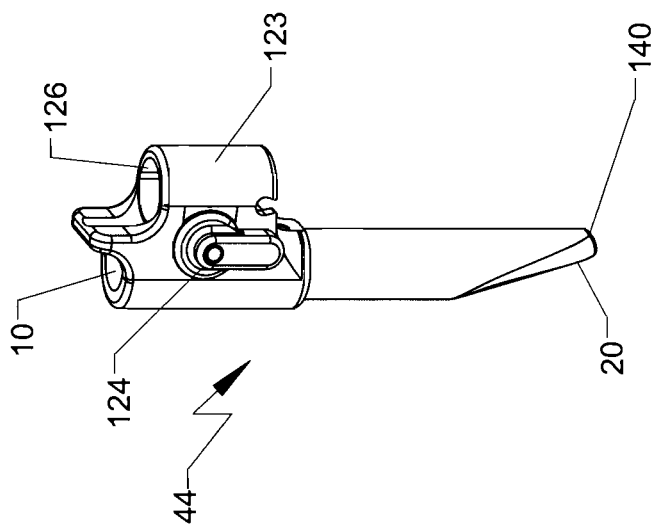
FIG. 17 is an isometric view of an adjunctive chamber.

Referring to FIGS. 9A-C, the dispenser cap is illustrated. The dispenser cap is used to close the end of the adjunct chamber frame 56 and to cooperate with the valve assembly 17 to cause the pressurized gas to be dispensed. In the preferred embodiment, the first end of the dispenser cap includes threads 70 which secure the dispenser cap to the adjunct chamber frame 56. Alternatively, adhesive, bayonet mount, friction fits or the like may be utilized to secure the dispenser cap to the adjunct chamber frame without departing from the scope of the invention. This is best seen in FIGS. 9 and 10, wherein the threaded cap 54 comprises an opening 27 and an engagement means, e.g. a valve aperture 55 to engage the canister and for delivery of metered doses of aerosol propellants. A restrictor jet 74 may be utilized to control the flow of gas through the outlet tube. The second end of the dispenser cap includes an outlet nozzle bore 72 sized to cooperate with the outlet nozzle 20 for positioning thereof. In the preferred embodiment, the outlet nozzle 20 is adhered or frictionally fit to the dispenser cap. The outlet nozzle 20 can be rigid, flexible or semi-flexible. The outlet nozzle 20 is tubular in construction, having a distal end 140 (FIG. 8) with an opening 52 that may, if desired, be defined by an insert, e.g. nozzle, venturi or the like, inserted into the opening 52 and having a particularly configured passageway to cause the anesthetic sprayed therefrom to spray in a desired pattern. The distal end of the nozzle 20 can be flexible, and may be bent by a physician into a desired angulation so that the anesthetic is sprayed in a desired location with respect to the location where the syringe needle will be inserted beneath the skin of the patient. The needle 5 can be varied in length, for example, shortened or elongated, so it extends beyond the distal termination of the outlet nozzle 20 so that the nozzle 20 doesn't interfere with insertion of the needle subcutaneously.

Figure 3:
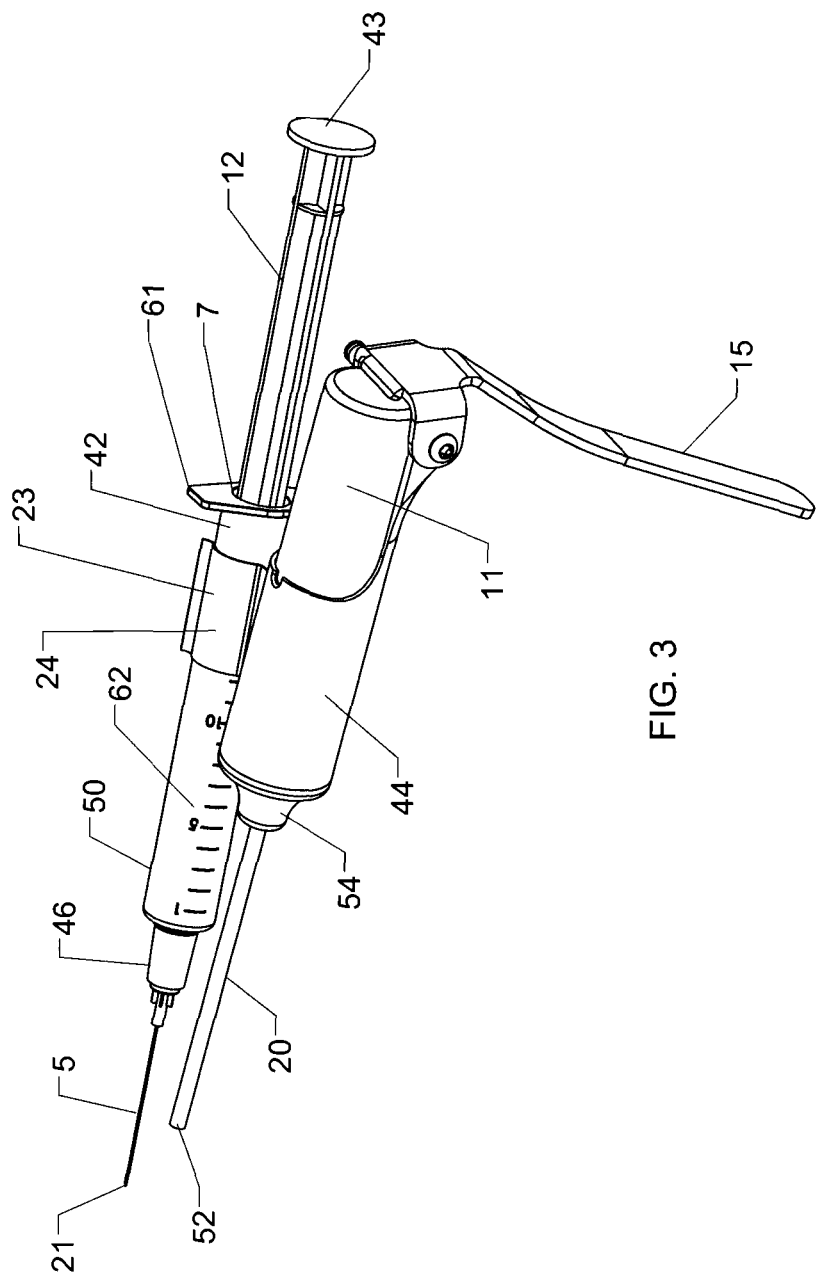
FIG. 3 is a perspective view illustrating an alternative embodiment of the present invention.

As shown in FIG. 3, a disposable syringe 42 is illustrated in conjunction with the module 44 of the present invention. The disposable syringe includes an elongated barrel 62 that is typically cylindrical in outer configuration, a plunger 12 having a thumb pad 43 or ring 13 (FIG. 1) that is engaged by the thumb or finger of the user, and a perpendicular tab 61 on the barrel 62 of the syringe 42 that is grasped by other fingers of the user while the ring or pad 13, 43 is being pushed to cause the plunger 12 to move in a direction toward the distal end 50 of the barrel 62. The plunger 12 pushes the medicament or liquid in the chamber 7 through the needle. The needle 5 is attached to the distal end of the syringe via a locking taper, luer lock 46, or the like, to allow fluid to flow into and through the needle 5. As is well known, the needle is thin and hollow, permitting the medicament within the chamber 7 to be dispensed therethrough. The needle 5 can be of any length so long as its distal end extends beyond the end of outlet nozzle 20.

In the various embodiments, the anesthetic comprises one or more gas, vapor or aerosol propellants. These propellants can be any type of aerosol propellants as long as they continue to decrease the temperature of the patient's skin or mucosal area targeted for an injection; examples are the aerosol propellants sold by DuPont Company, Wilmington, Del., under the trade names DYMEL™ 134a and DYMEL™ 227a. In preferred embodiments, the anesthetic comprises a blend of two aerosol propellants in varying percentages of weight/weight (w/w). The range of DYMEL™ 134a can be from about 0.001% to 99.999% w/w and the weight of DYMEL™ 227a can be from about 0.001% to 99.999% w/w. In other embodiments, one or more compounds, pharmaceutical grade compounds or compositions can be included, for example, compounds which alter the vapor pressure of the gas or vapor being emitted. Pharmaceutical compounds include, for example, antimicrobial, taste altering compounds or flavoring compounds, e.g. menthol, mint, etc., therapeutically effective compounds and the like. In preferred embodiments, the aerosol propellants (e.g. DYMEL™ 134a, DYMEL™ 227a) are pharmaceutical grade and shown to be safe for inhalation, ingestion, and for use in sensitive areas of a patient, e.g. eyes, lips, nose etc. These pharmaceutical grade aerosol propellants can be obtained from DuPont Company, Wilmington, Del.

The anesthetic is preferably contained within a small or specialized canister of the type typically utilized for metered dose inhalers (e.g., asthma) and includes a deep drawn metal canister constructed from a metal such as aluminum or steel. The deep drawn canister 11 (FIG. 4D) includes a valve assembly 17 crimped and sealed within the open end of the metal canister to create a sealed pressure canister that is light weight and portable. The aerosol propellants are contained within the metal canister under pressure so that depression of the dispenser tube 58 releases the propellant through the valve assembly. In operation, the dispenser tube 58 of the valve assembly 17 may be operated in a variety of manners which may include, but should not be limited to, finger nozzles, levers, cams, solenoids or the like, which permit the valve to be depressed for release of the propellant.

Figure 5A:
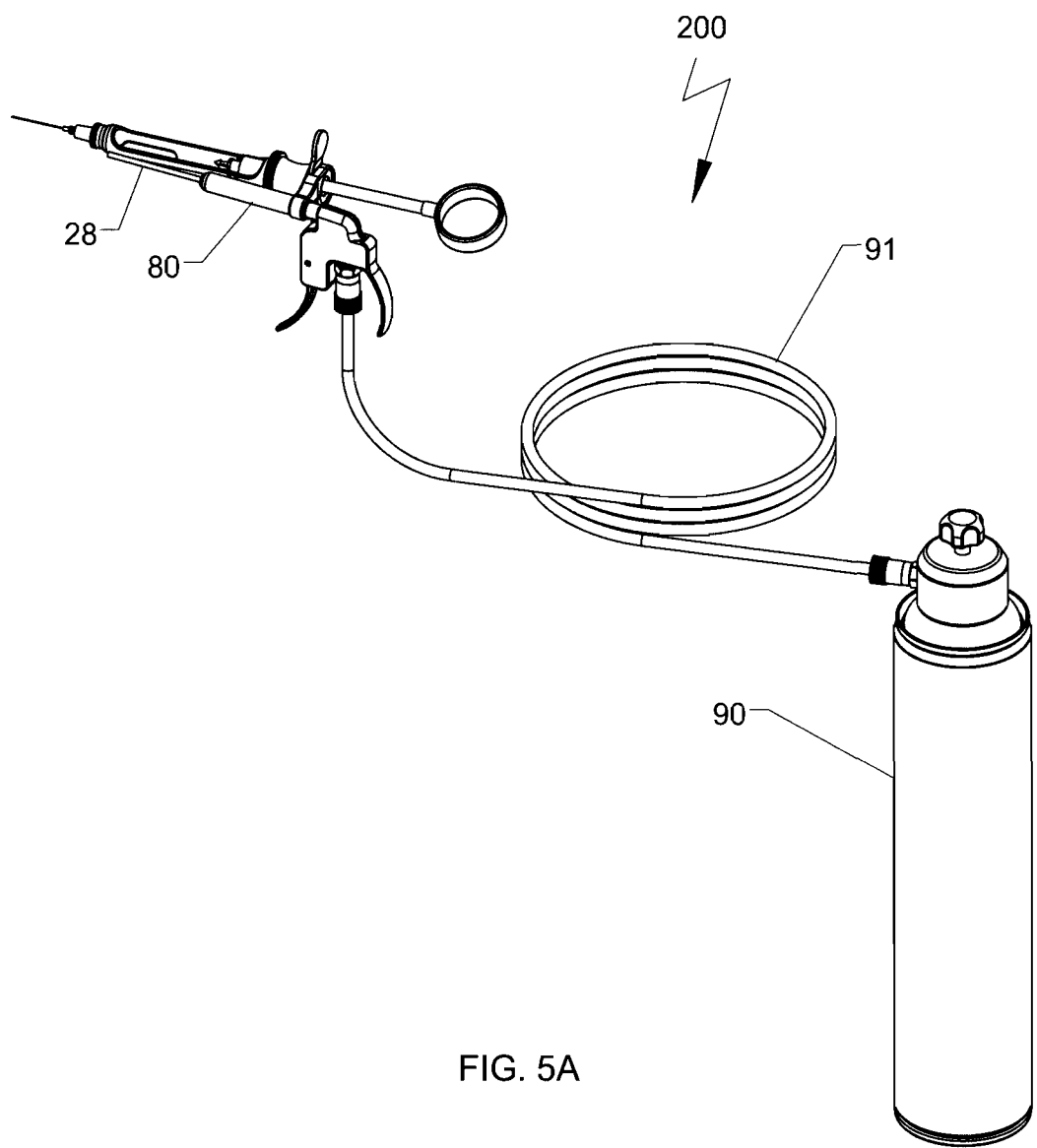
FIG. 5A is a perspective assembly view illustrating an alternative embodiment of the present invention having a remote tank for holding an endothermic gas or vapor.
Figure 5B:
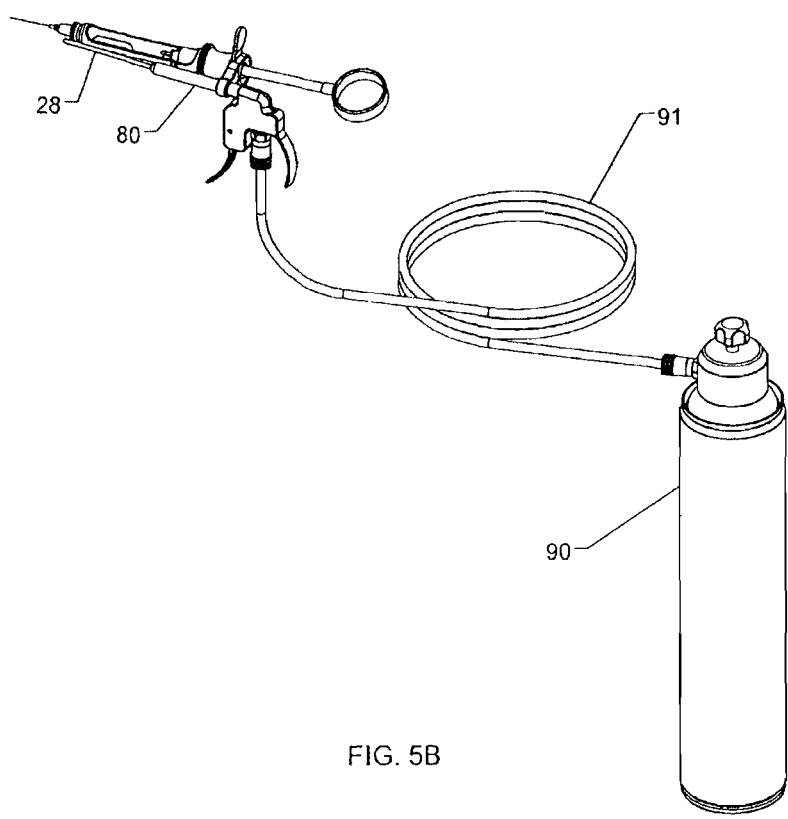
FIG. 5B is a perspective assembly view illustrating an alternative embodiment of the present invention having a remote tank for holding an endothermic gas or vapor.
Figures 5C, 5D:
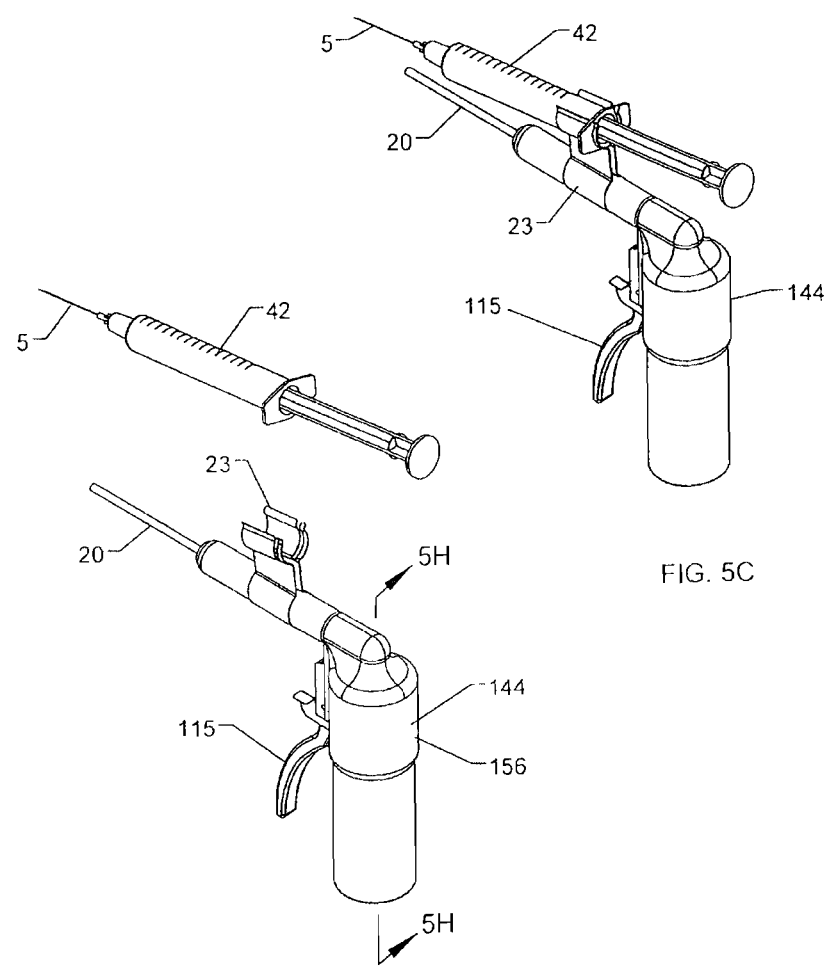
FIG. 5C is a perspective view of an alternative embodiment of the present invention.
FIG. 5D is a partially exploded view of the embodiment illustrated in FIG. 5C.
Figures 5E, 5F:
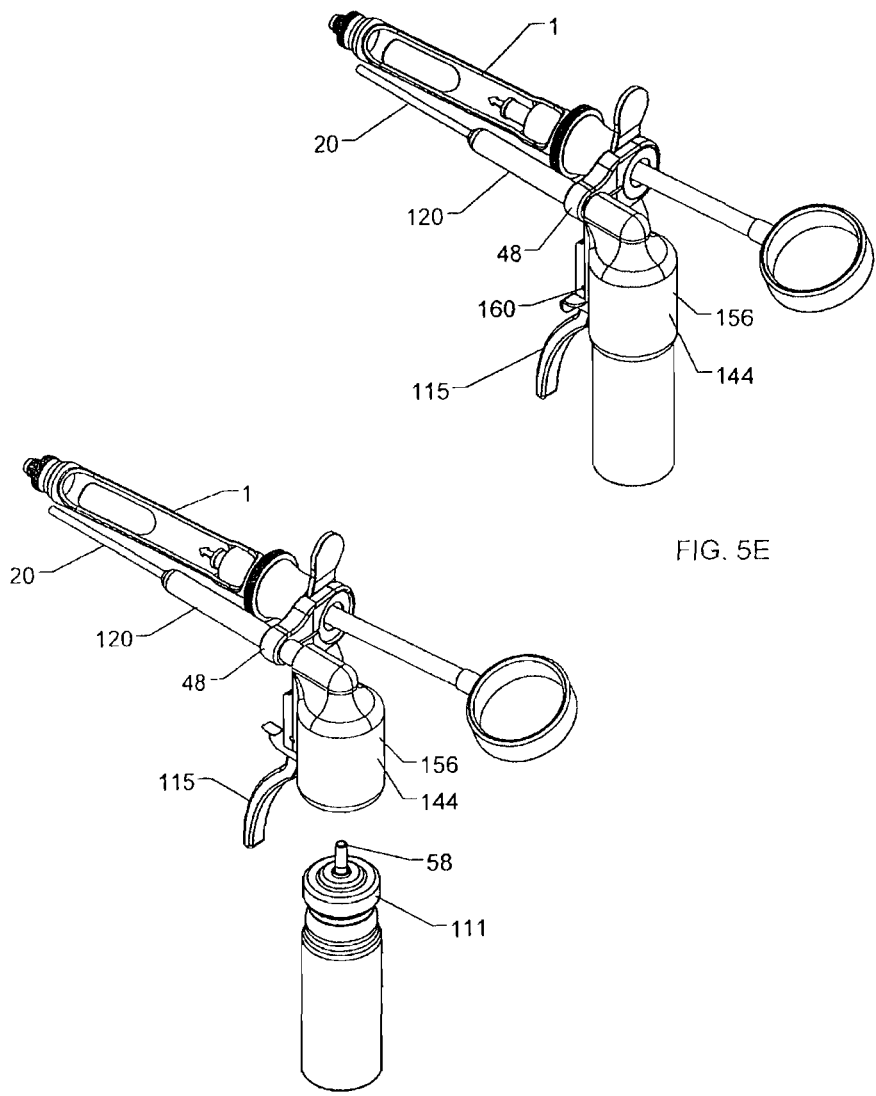
FIG. 5E is a perspective view of an alternative embodiment of the present invention.
FIG. 5F is a partially exploded view of the embodiment illustrated in FIG. 5E.
Figure 5G:
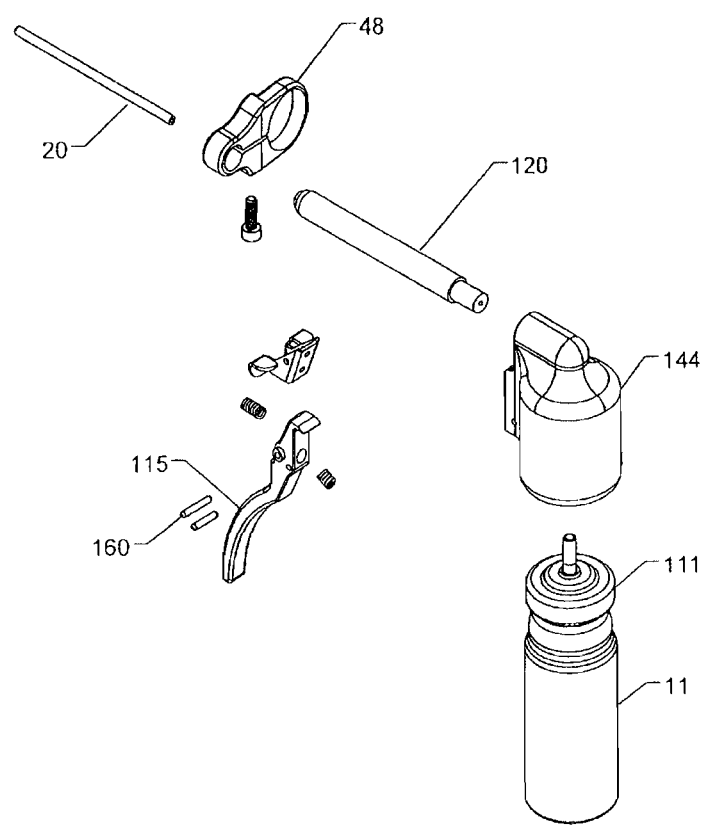
FIG. 5G is an exploded view of the embodiment illustrated in FIG. 5E.
Figure 5H:
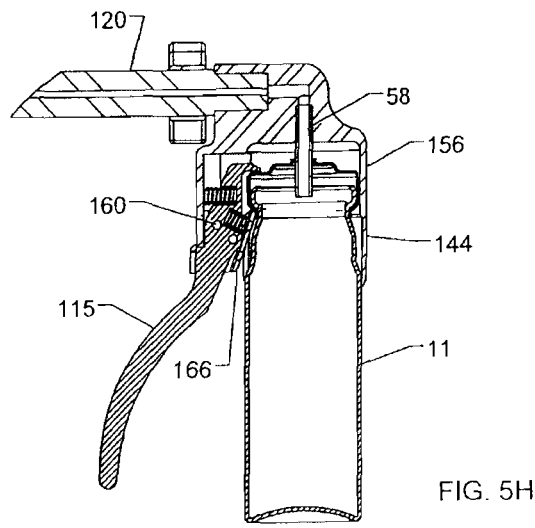
FIG. 5H is a section view taken along lines 5H-5H of FIG. 5D.
Figure 5I:
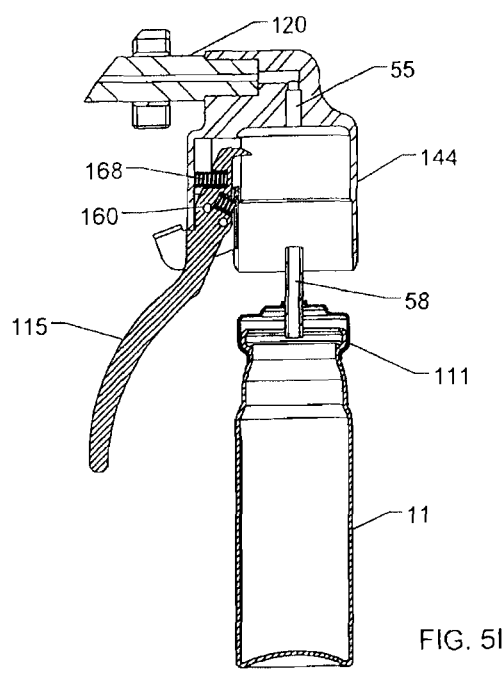
FIG. 5I is a partially exploded view of the embodiment illustrated in FIG. 5H.
Figure 5J:
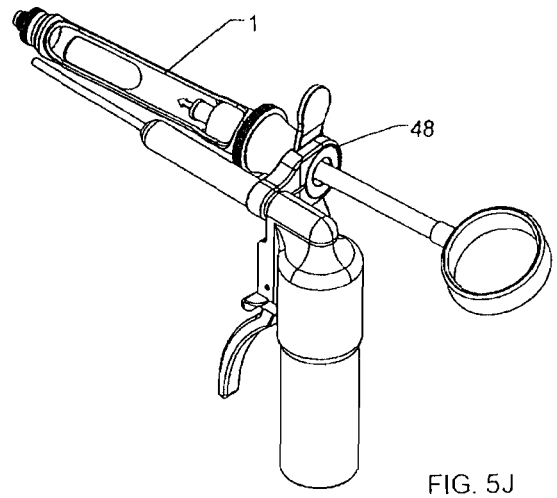
FIG. 5J is a perspective view of an alternative embodiment of the present invention.
Figure 5K:
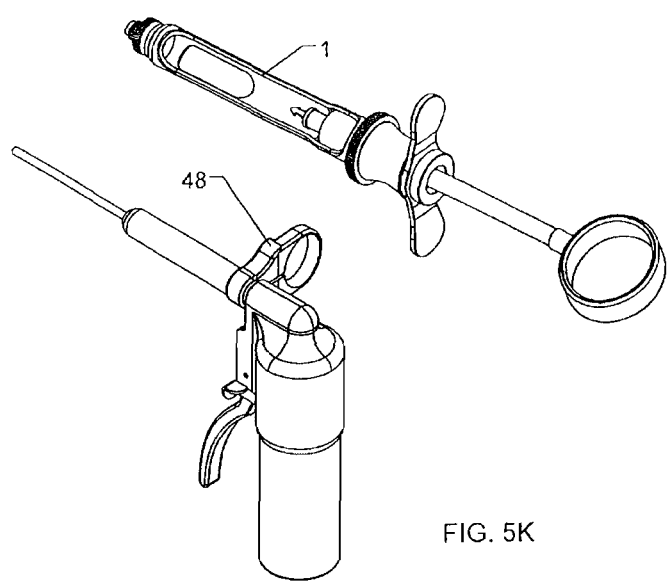
FIG. 5K is a partially exploded view of the embodiment illustrated in FIG. 5J.

The location on the surface area of the patient where an injection is to take place is determined, and the syringe 42 with the module 44 attached thereto is positioned at a desired location and angle of skin penetration approximately 1 to 2 centimeters above the skin. The lever 15 is depressed to engage the valve to permit flow of the anesthetic, e.g. an aerosol propellant (vapo-coolant), for a period of time, such as 1 to 3 seconds. The skin is then penetrated by the needle 5 of the syringe 42 to a desired depth and the medicament is injected to numb in a separate location either while the aerosol propellant is flowing, or just after the flow of the aerosol propellant is stopped. Injections may be first subcutaneous, then intramuscular or intradermal. The anesthetic can be administered at various depths in sequence of the dermal layers to make sure that the area is numb, such that a patient will not feel any pain when the needle, e.g. i.v. injection is inserted. In some embodiments, the first dermal or skin layer is numbed first, and then the next layer etc., in sequence. If desired, the needle may be retracted a desired distance, with additional injection occurring, or may be removed so that the next location can be chosen. During the step-wise process of injection including multiple injections at the same site of needle penetration, additional aerosol propellants may be dispensed as desired to maintain the numbness of the skin at that location. If, during the process of injection, the canister 11 runs out of anesthetic, e.g. an aerosol propellant, it may be removed from the adjunct chamber frame 56 and replaced with a replacement canister. In embodiments where a large area is targeted for numbing, a larger volume or quantity of aerosol propellant in a large canister 90 can be utilized so as not to contaminate the field or location and to prevent cross contamination (FIGS. 5A, 5B). In some embodiments, the apparatus comprises an assembly 200 (FIGS. 5A, 5B) which is attachable to a user's clothes or belt, or a back-pack carrying any further number of doses of propellant. In this manner, the user is not required to replace a spent canister. The assembly 200 is connected to the remote valve assembly 80 via a long flexible tube 91 which can be extended or retracted as needed by the user, and is actuated in a similar manner as with the smaller canister 11, or the tube is connected to the canister, thereby providing a reservoir of aerosol propellant. The canister may also be refillable, and may additionally include regulators or the like known in the art for reducing pressure from large high pressure tanks. When the injection process is completed, the syringe 42 may be removed from the clip portion 23 and suitably discarded, and the module 44 may be re-used with other syringes or for single use per point to prevent cross-contamination. It should also be noted that while the preferred embodiment entails placing the large canister in a fixed position, the canister may optionally include an attachment means for securing the canister to the belt or back of the user to provide mobility to the user while still providing the added capacity of the larger canister.

As such, in this way the present invention provides an effective way of dispensing an anesthetic onto the skin of a patient where an injection is to take place so that the injection is painless. The present invention is not limited for use in association with injections in the face for aesthetic enhancement. Rather, it may be used as an attachment to any syringe or other injection device used to inject any medication for any purpose. For example, the inventive device may be used with injection devices associated with diabetes glucose monitors, BOTOX®, hair transplants, multiple needle allergy introducers and the like.

Figure 1:
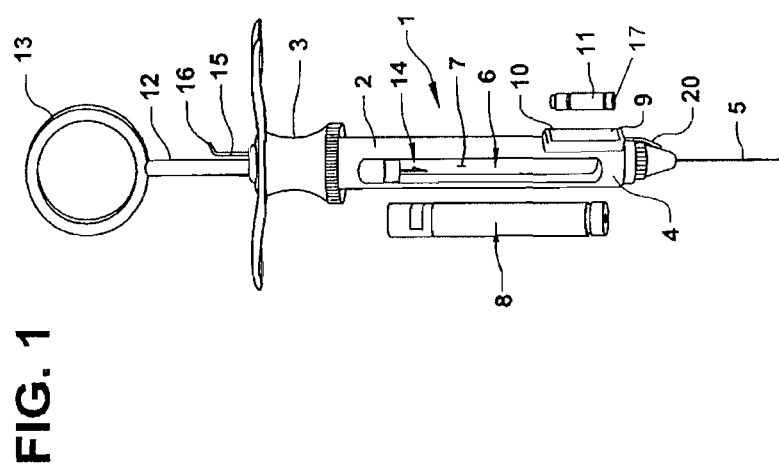
FIG. 1 is a plan view of the dental syringe with the cartridge and canister removed therefrom.

Referring to FIGS. 1 and 2, the apparatus comprises an elongated tubular housing 1 having an outer wall 2, an upper end 3, a substantially hollow interior, and a lower end 4 having an injection needle 5 extending therefrom. On the housing outer wall is an elongated opening 6 in communication with an anesthetic chamber 7 formed within the housing interior. The anesthetic chamber receives a cartridge 8 having a conventional dental anesthetic stored therein.

The outer wall 2 can also include a smaller opening 9 (FIG. 1) which is utilized as the receptacle or adjunctive chamber 10 for receiving a canister 11 (FIG. 2). The canister 11 includes an endothermic gas or vapor, or "freeze spray" solution that rapidly absorbs heat when dispersed into the atmosphere. Coaxially received within the anesthetic chamber is a plunger 12 having a thumb ring 13 or other means for pushing the plunger at an upper end.

Coaxially received within the adjunctive chamber 10 is a depressible trigger 15 having a handle 16 at an upper end that protrudes from the upper end of the housing. Depressing the trigger propels the gaseous or vapor propellant through an outlet nozzle 20 on the lower end of the housing. The nozzle 20 is oriented to project a stream of gas or vapor along a delivery axis that intersects a delivery axis of the needle, preferably at a point immediately adjacent to the needle outlet 21. Accordingly, a practitioner can first deaden a proposed injection site and then immediately insert the needle with little movement or repositioning of the syringe.

Figure 6:
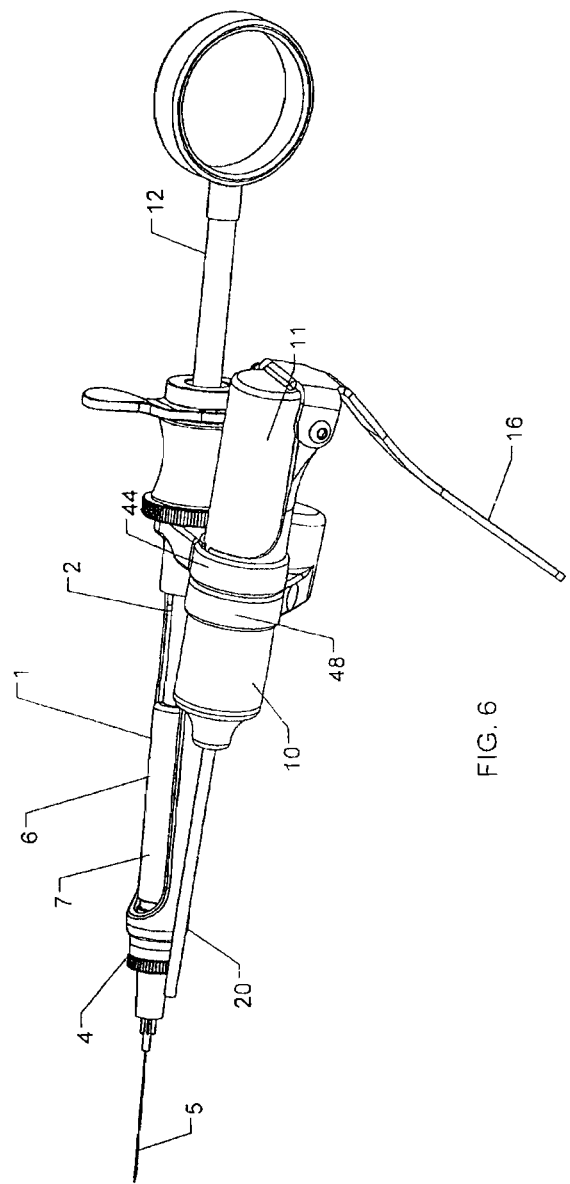
FIG. 6 is a plan view of a syringe with the canister installed in the module or adjunctive chamber.
Figure 7:
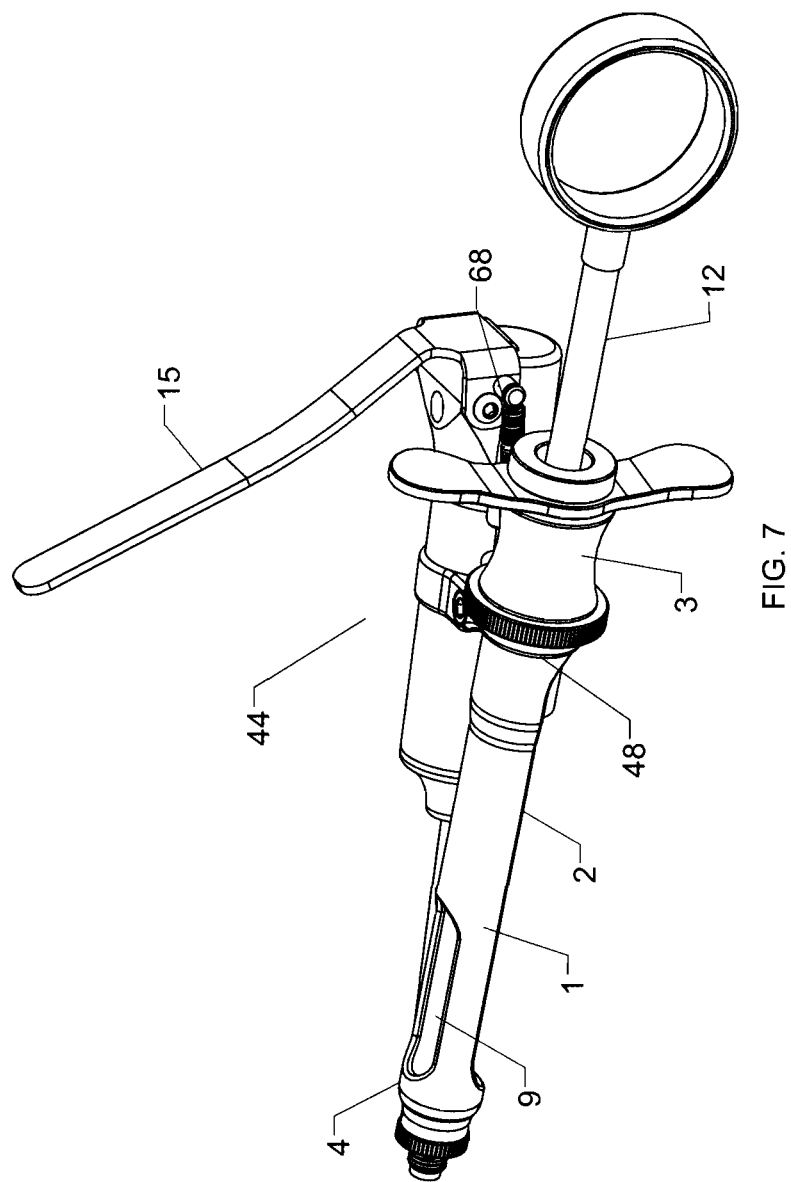
FIG. 7 is a perspective view of the embodiment illustrated in FIG. 6.

Referring to FIGS. 6-8, an alternative embodiment of the present device is illustrated. This embodiment utilizes a reusable syringe in combination with the module 44 and the sleeve 48 for attaching the module to the syringe. This embodiment also illustrates that the module and the sleeve may be constructed from metal without departing from the scope of the invention.

In some embodiments, the module 44 may be constructed and arranged to accommodate two or more canisters 11. The arrangement of the two or more canisters or modules can be arranged in any manner and can be of varying dimensions and shapes. For example, the modules can be attached together. In some embodiments, the modules 44 are arranged to be on either side of the syringe. One of ordinary skill in the art can envisage possible combinations, locations, patterns and designs for the receptacles.

Referring to FIG. 8, the container or canister 11 which contains one or more gases or vapors comprises a neck 111 having an end cap 112 and a dispenser tube 58 dimensioned for slidable insertion and engagement of the dispenser cap 54 of the module 44 (FIG. 8). The canister contents can be any type of anesthetic. In some embodiments, the anesthetic comprises one or more gases (vapors); examples include, without limitation, aerosol propellants, endothermic gases (vapors) and refrigerants that rapidly absorb heat when released from pressure to the atmosphere and the like. Accordingly, a user can initially disperse the gas or vapor composition onto the injection site to minimize any pain and discomfort associated with an injection. Subsequently, the practitioner inserts the needle into the deadened site (blanched) and injects the contents of the syringe. As discussed above, the receptacle can be of any size and shape to accommodate canisters or containers of varying sizes and shapes. The size of the canisters used depends on the volume of the anesthetic, e.g. gas or vapor needed for the particular procedure. Different blends produce different temperatures; therefore, the doctor in charge can decide which of the blends to utilize for the necessary effect. In some embodiments, the temperature of the gas or vapor when administered is above freezing temperature to avoid necrosis, frost bite, pain, discomfort or any type of biological damage to the area of administration. Since the medical caregiver, e.g. doctor, controls the delivery of the anesthetic, e.g. gas or vapor, the doctor is in charge of the delivery of the gas or vapor to enhance the patient comfort, therefore, the doctor can add additional bursts if the patient informs the doctor that more is needed.

Referring to FIGS. 5C-K, an alternative embodiment of the present invention is illustrated. In this embodiment, the module 144 is constructed and arranged to be secured to the syringe 42 in a perpendicular arrangement with respect to the syringe. The adjunct chamber frame 156 is still constructed to allow the insertion of a portion of the canister 11. The distal end of the adjunct chamber frame 156 includes the dispenser tube shoulder 55 for accepting the dispenser tube 58. In this embodiment, the trigger 115 is constructed and arranged to cooperate with the neck 111 of the canister 11 to provide controlled dispensing of the pressurized gas. The trigger 115 is provided with a pivot pin 160 which allows the ram 166 to catch under the neck to cause the canister to move within the adjunct chamber frame. Return spring 168 returns the trigger to its original position. An outlet tube 120 extends out of the adjunct chamber frame 156 at an angle that is substantially perpendicular with respect to the canister 11. The outlet tube 120, therefore, provides a body to cooperate with the sleeve 48 or clip 23 for ready attachment to reusable or disposable syringes. The outlet tube 120 also functions to secure and position the outlet nozzle 20, which may be telescopingly engaged to the outlet tube to allow the length of the outlet nozzle to be adjusted.

It should also be noted that, while not shown, a small laser light or the like may be secured to the module 44, 144 to indicate the trajectory of the pressurized gas. In this manner, the user would be provided with a visual guide to where the gas will strike the patient's skin.

The above-described device is not limited to the exact details of construction and enumeration of parts provided herein. For example, the receptacle could comprise separate components, e.g. a separate clip that is attachable to the receptacle and to any conventional syringe. The endothermic gas or vapor should remove sufficient heat to function as described without causing necrosis. The concentration and volume of the propellant components can be varied to deliver small doses of highly-concentrated substances, or a prolonged, continuous dispersal of diluted substances. The canister can also be color coded for varying temperatures produced by the different blends or aerosol propellants. In addition, gas or vapor delivery can be automated with a laser mechanism that dispenses gas or vapor when the needle is within a minimal distance from the skin and automatically disables gas or vapor flow upon needle penetration. Accordingly, a practitioner can rapidly inject multiple sites. Finally, although the device has been primarily described and depicted as a syringe, the gas or vaporous canister could have other uses. For example, it could be attached to a scalpel blade to allow a quick, painless incision when performing certain procedures, such as removing moles. Furthermore, the size, shape and materials of construction of the various components can be varied.

Referring to FIGS. 13A-B, 14-19 and 20A-D, alternative embodiments of the present invention are illustrated. In these embodiments, an apparatus comprising a module 44 is removably attached to an autoinjector syringe barrel 162, and accommodates a canister 11 comprising a gaseous (vapor) anesthetizing composition. The module 44 includes an elongated outlet nozzle 20 for directing the gaseous (vapor) anesthetizing composition to intersect with the delivery axis 30 of the needle 5. The module includes an adjunct chamber frame 56, attachment means in the form of a securable clip 123 or a sleeve 48, a latch 124, an outlet nozzle 20 and a dispenser cap 54. The adjunct chamber frame 56 functions to secure the adjunct chamber to the autoinjector syringe barrel 162, and contains the canister 11 as well as the securable clip(s) 123 and the dispenser cap 54. In this embodiment, the canister base 111 functions as the trigger member 15 (FIG. 12A-E) functions to dispense the contents of the canister 11 containing the anesthetic composition by forcing the canister to slide within the adjunctive chamber 10 of the adjunct chamber frame 56. During the sliding action, the dispensing tube 58 of the canister 11 is pressed against the dispenser tube shoulder 55 to cause the canister valve 17 to open, allowing compressed gas to escape through the dispenser tube 58. The canister 11 of the cartridge 8 is frictionally secured within the adjunct chamber frame 56 to allow the sliding action. Pressure and/or springs within the valve assembly 17 function to stop the flow of gas when pressure is released from the base of the canister 111 or the trigger 15. Latch pivot pins 125 cooperate with latch pivot pin apertures 127 in the adjunct chamber frame 56 to allow the securable clip 123 to be pivoted between an open position FIG. 13B and a closed position around the autoinjector syringe 162 FIG. 14. In some embodiments, the module 44 is disposable. In other embodiments, the autoinjector syringe 162 is disposable. In yet other embodiments, the canister 11 is disposable. In other embodiments, any one or combination of parts of the apparatus is disposable.

Still referring to FIGS. 13A-B, 14-19 and 20A-D, the module 44 includes an adjunctive chamber 10 for accepting a gas cartridge 8 in the form of a canister 11. The outer diameter of the module includes an attachment means which may comprise a securable clip 123 which is adapted to cooperate with the outer diameter of an autoinjector syringe barrel 162 for securing the module to the autoinjector syringe. The securable clip 123 preferably includes a pair of arcuate members 126 made of a resilient or rigid material so that the arcuate members may be closed around the outer diameter of the autoinjector syringe barrel 162 and latched in place via latch 124. The latch 124 is rotatably secured to the adjunct chamber frame 56 to allow the latch pin 128 to engage the latch slot 130. In this manner, the module may be securely attached to autoinjector syringe barrels to prevent slippage during use. In at least one embodiment, orientation tabs are provided to insure a preferred orientation between the autoinjector syringe 162 and the module 44.

Figure 18:
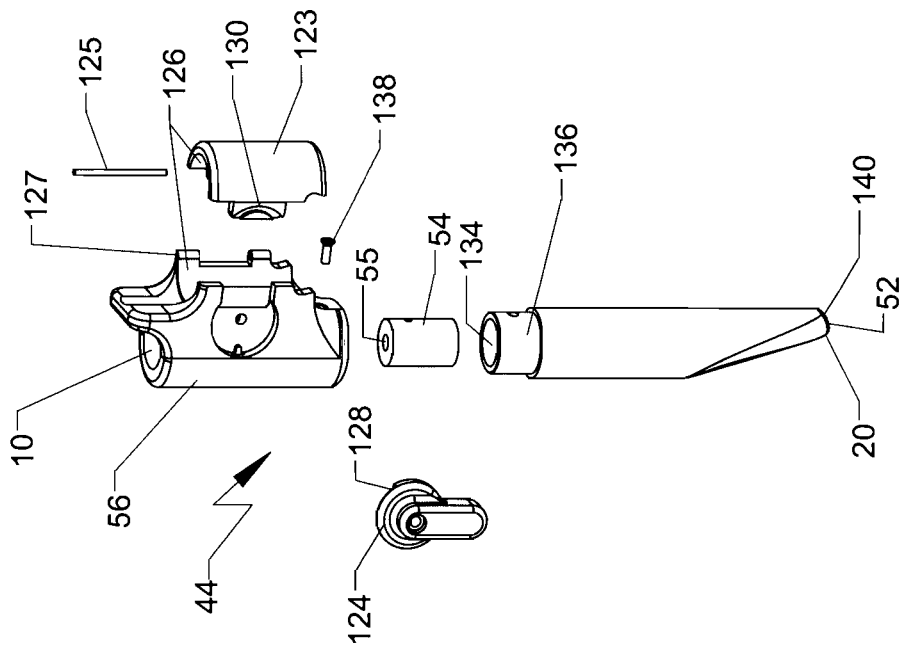
FIG. 18 is an exploded view of the adjunctive chamber of FIG. 17.

Referring to FIG. 18, one embodiment of the dispenser cap 54 is illustrated. The dispenser cap is used to close the end of the adjunct chamber frame 56 and to cooperate with the valve assembly 17 to cause the pressurized gas to be dispensed. In the preferred embodiment, the outlet nozzle 20 includes a pocket 134 sized to contain the dispenser cap. A pilot shaft 136 is utilized to align and secure the dispenser cap to the adjunct chamber frame 56 via fastener 138. Alternatively, adhesive, bayonet mount, friction fits or the like may be utilized to secure the dispenser cap to the adjunct chamber frame without departing from the scope of the invention. A restrictor jet 74 (FIG. 9C) may be utilized to control the flow of gas through the outlet tube. The second end of the dispenser cap includes an outlet nozzle bore 52 sized to cooperate with the outlet nozzle 20 for directing the flow of gas. The outlet nozzle 20 of the preferred embodiment is rigid; however, flexible or semi-flexible outlet nozzles may be utilized without departing from the scope of the invention. The outlet nozzle 20 is tubular in construction, having a distal end 140 with an opening 52 (FIG. 8) that may, if desired, be defined by an insert e.g. nozzle, venturi or the like, inserted into the opening 52 and have a particularly configured passageway to cause the anesthetic sprayed therefrom to spray in a desired pattern. The distal end of the nozzle 20 can be flexible, and may be bent by a physician into a desired angulation so that the anesthetic is sprayed in a desired location with respect to the location where the syringe needle will be inserted beneath the skin of the patient. The needle 5 can be varied in length, for example, shortened or elongated, so it extends beyond the distal termination of the outlet nozzle 20 so that the nozzle 20 doesn't interfere with insertion of the needle subcutaneously.

Figure 19:
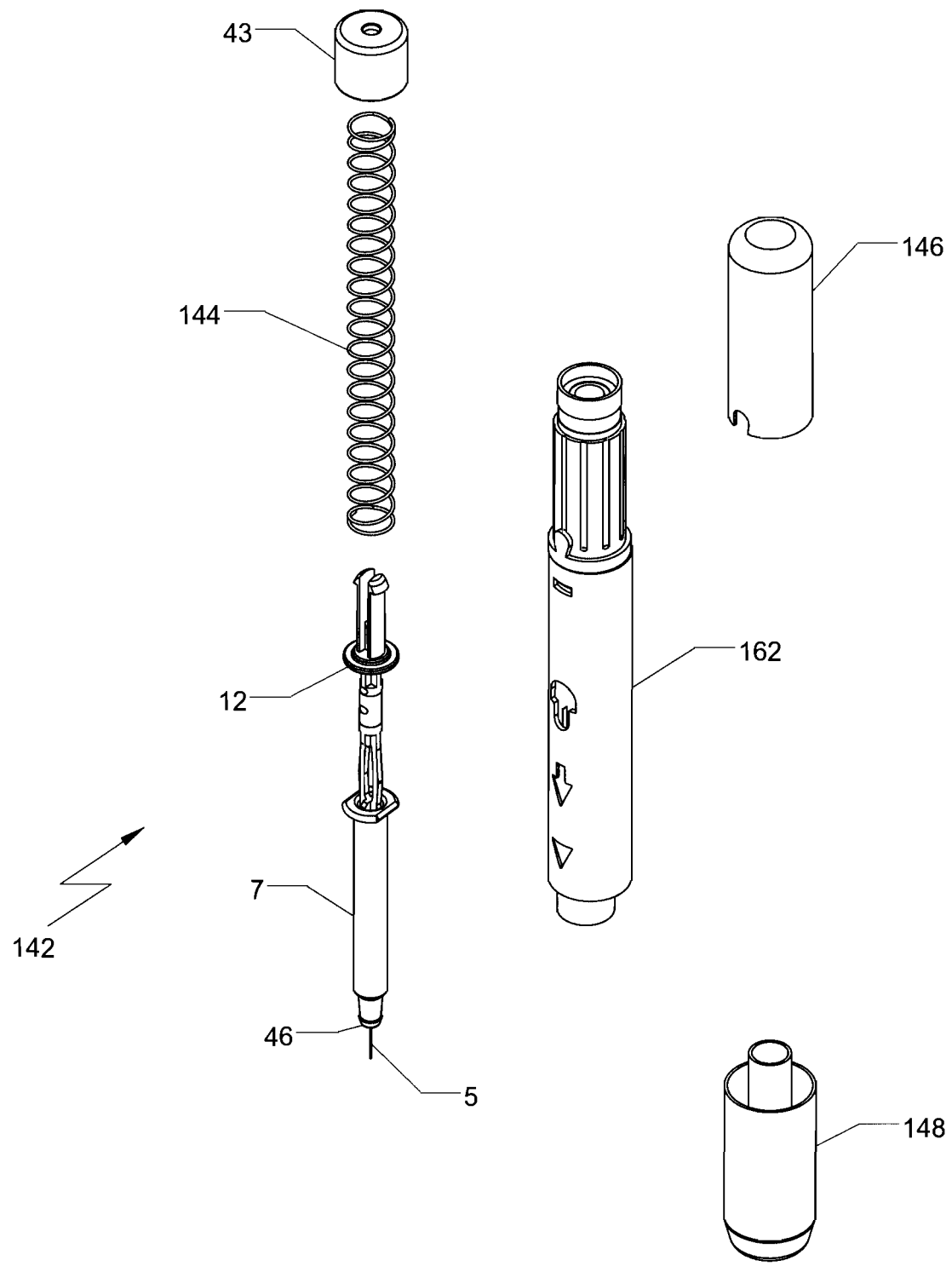
FIG. 19 is an exploded view of an autoinjector syringe.
Figure 20:
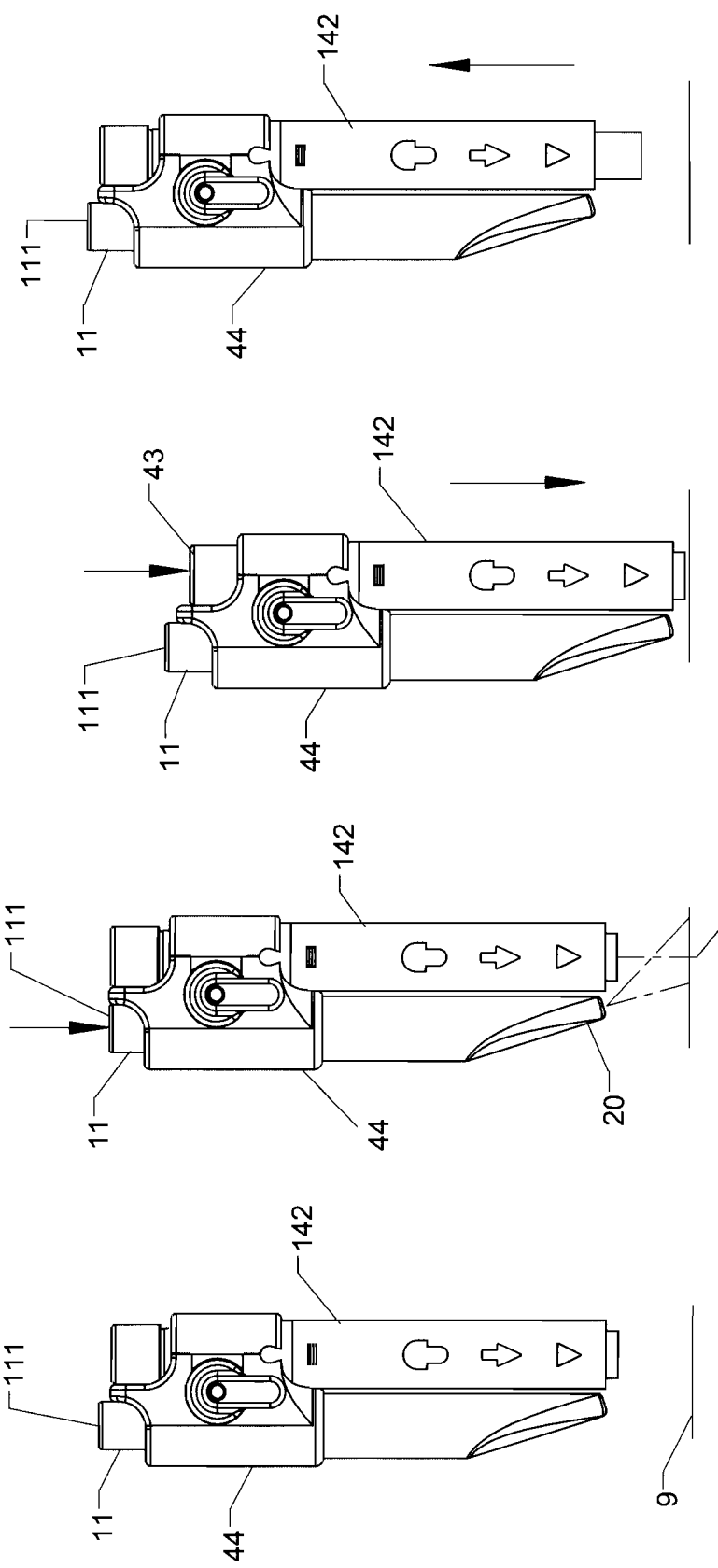
FIG. 20A is an assembled view of the autoinjector syringe and an adjunctive chamber illustrating a method of using the assembly.
FIG. 20B is an assembled view of the autoinjector syringe and an adjunctive chamber illustrating a method of using the assembly.
FIG. 20C is an assembled view of the autoinjector syringe and an adjunctive chamber illustrating a method of using the assembly.
FIG. 20D is an assembled view of the autoinjector syringe and an adjunctive chamber illustrating a method of using the assembly.
Figure 21:
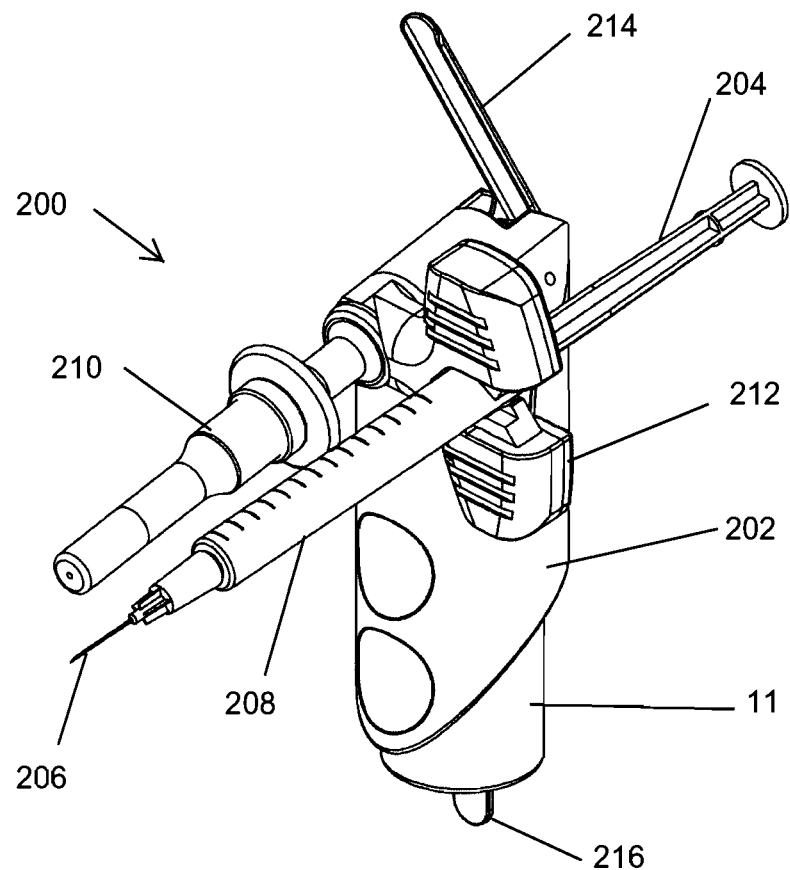
FIG. 21 is a perspective view of an illustrative embodiment of an applicator for dispensing a fluid, such as an anesthetic, shown with a syringe attached thereto.
Figure 22:
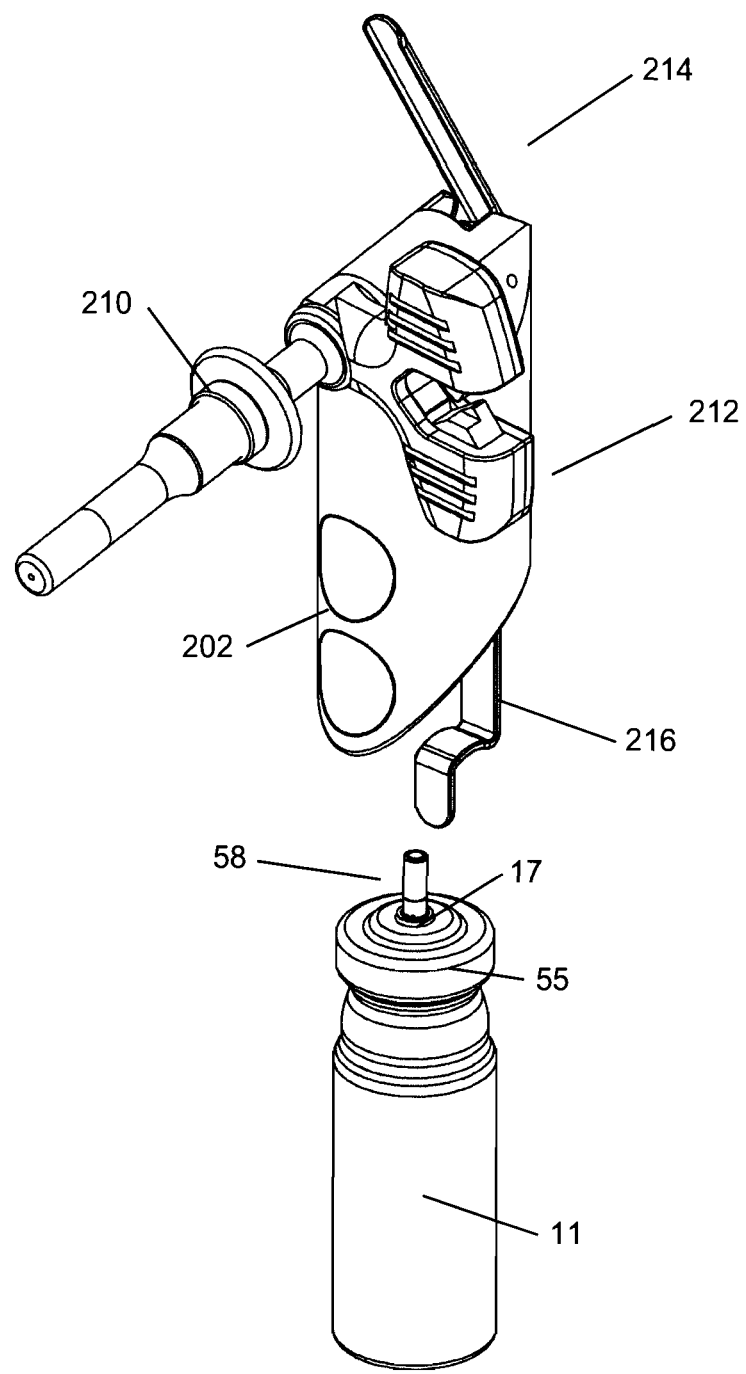
FIG. 22 illustrates the applicator for dispensing a fluid shown in FIG. 21, with a canister prior to be inserted therein, and shown without the attached syringe.
Figure 23:
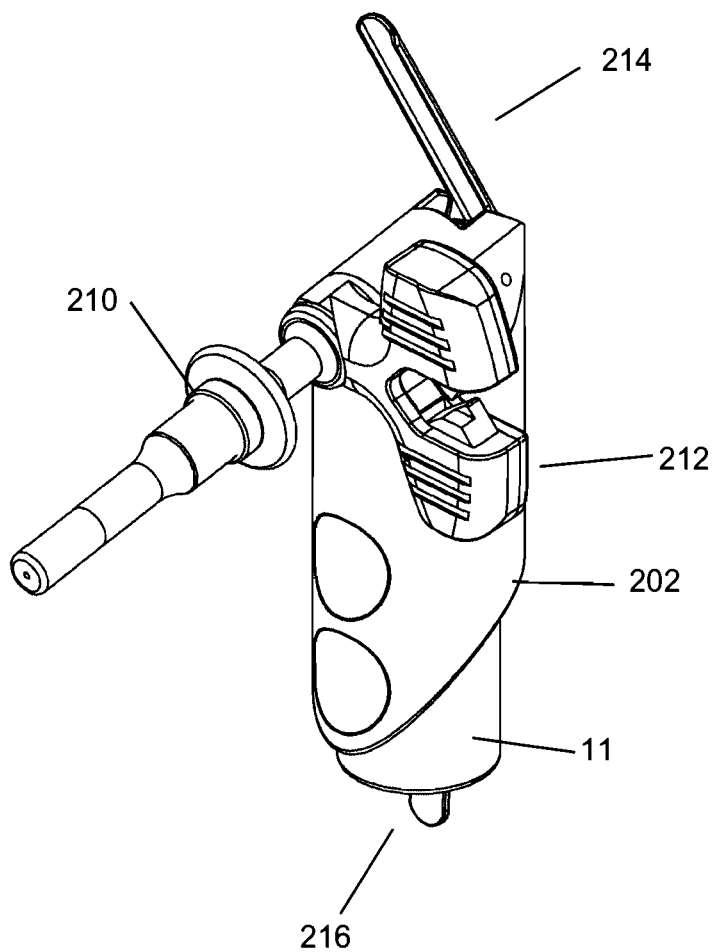
FIG. 23 illustrates the applicator for dispensing a fluid shown in FIG. 21, with the canister inserted therein, and shown without the attached syringe.
Figure 24:
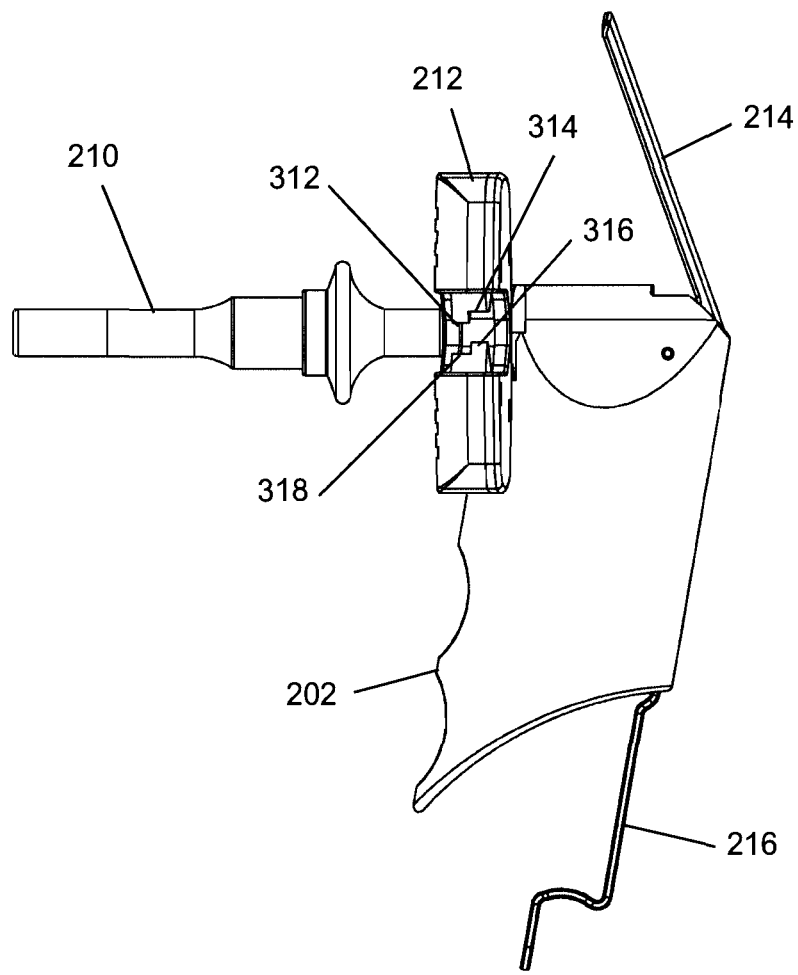
FIG. 24 is a side view of the applicator for dispensing a fluid shown in FIG. 21.
Figure 25:
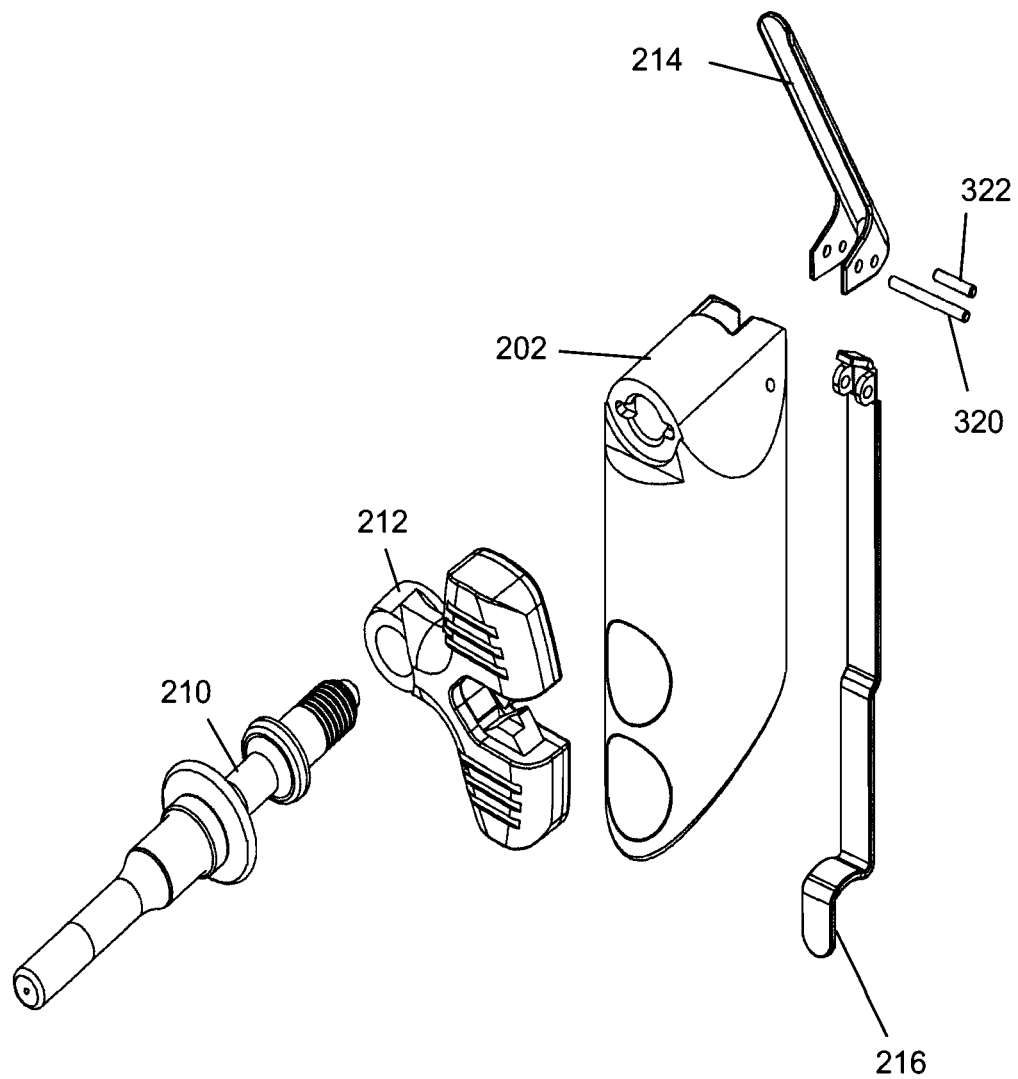
FIG. 25 is an exploded view of the applicator for dispensing a fluid.

Referring to FIG. 19, an exploded view of an autoinjector syringe 142 is illustrated in conjunction with the module of the present invention. The autoinjector syringe 142 includes an elongated barrel 162 that is typically cylindrical in outer configuration, a plunger 12 having a thumb pad 43 or ring 13 (FIG. 1) that is engaged by the thumb or finger of the user to cause the plunger 12 to move in a direction toward the distal end 50 of the barrel 162 via spring member 144. The plunger 12 pushes the medicament or liquid in the chamber 7 through the needle. The needle 5 is attached to the distal end of the syringe via locking taper, press fit, luer lock 46 or the like, to allow fluid to flow into and through the needle 5. As is well known, the needle is thin and hollow, permitting the medicament within the chamber 7 to be dispensed therethrough. The needle 5 can be of any length so long as its distal end extends beyond the end of outlet nozzle 20. A top cap 146 and a needle cap 148 may be included with the autoinjector syringe to prevent inadvertent activation of the autoinjector syringe during shipping and travel. This construction permits the autoinjector syringe to be preloaded and carried for use as needed.

Referring to FIGS. 20A-D, operation of the autoinjector syringe with the module secured thereto is illustrated. If included, the top cap 146 and needle cap 148 are removed prior to placing the autoinjector syringe above the injection area 9 (FIG. 20A). The base portion 111 of the canister 11 is pressed, causing the valve assembly 17 to be opened and allowing the pressurized gaseous anesthetic to be directed through the nozzle 20 to the skin, thereby numbing the injection site (FIG. 20B). The thumb pad 43 is pressed after the autoinjector syringe 142 is placed onto the injection area (FIG. 20C). Once the injection is complete, the autoinjector syringe and module assembly are lifted away from the injection site as normal (FIG. 20D).

Referring to FIGS. 21-25, an alternative embodiment of the present invention relating to the method and apparatus of applying an anesthetic is shown. In this embodiment, an apparatus, referred to generally as applicator 200, comprises a module 202 configured to be secured or attached to a syringe 204, with needles 206, preferably secured or attached to the syringe barrel 208, and is designed to accommodate a canister 11 comprising a gaseous (vapor) anesthetizing composition. The applicator 200 may further include a dispensing member 210, a syringe barrel securing device 212, a dispensing trigger 214, and a canister lift lever 216. The dispensing member 210 may be integrally formed from, or attached to, a portion of the module 202.

Figure 26:
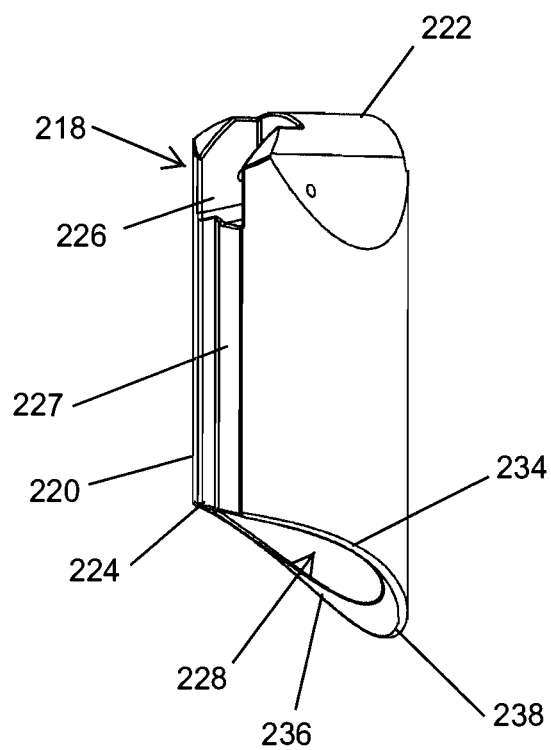
FIG. 26 is a perspective view of the module chamber frame.
Figure 27:
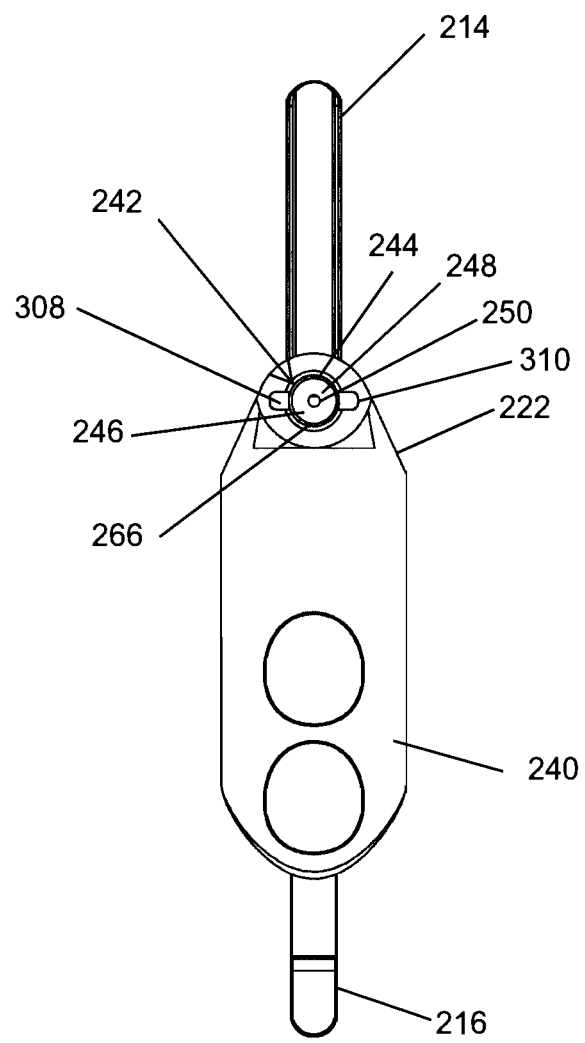
FIG. 27 is a front view of the applicator for dispensing a fluid shown in FIG. 21, illustrated without the dispensing member or syringe barrel securing device.
Figure 28:
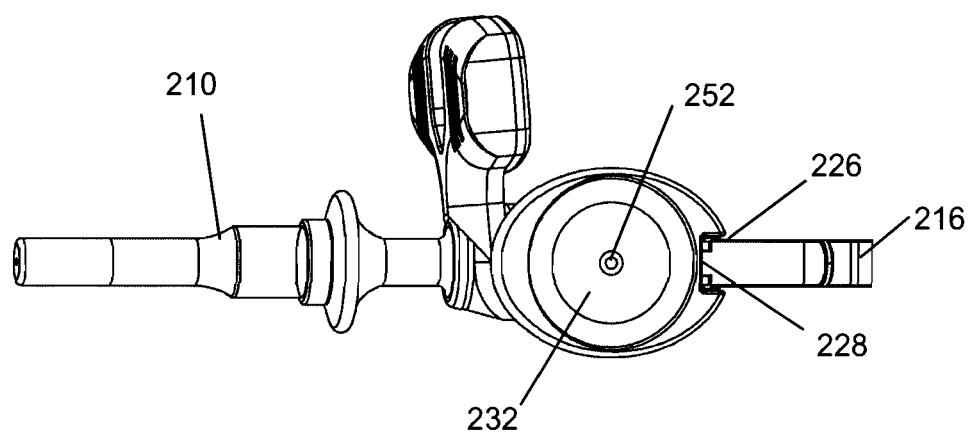
FIG. 28 is a bottom view of the applicator for dispensing a fluid shown in FIG. 21, illustrated without an inserted canister.
Figure 29:
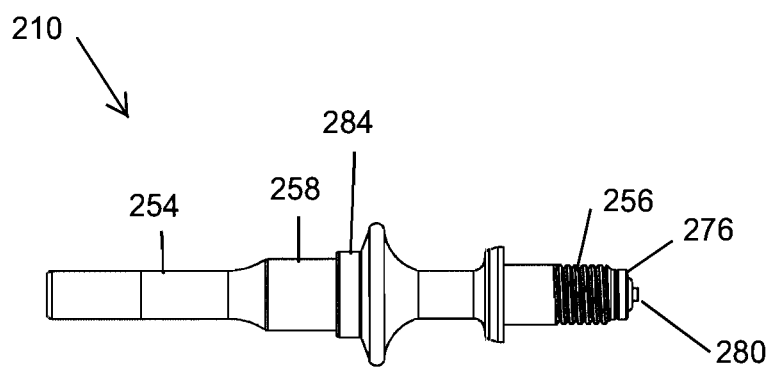
FIG. 29 is an illustrative example of a dispensing member.
Figures 30, 31:
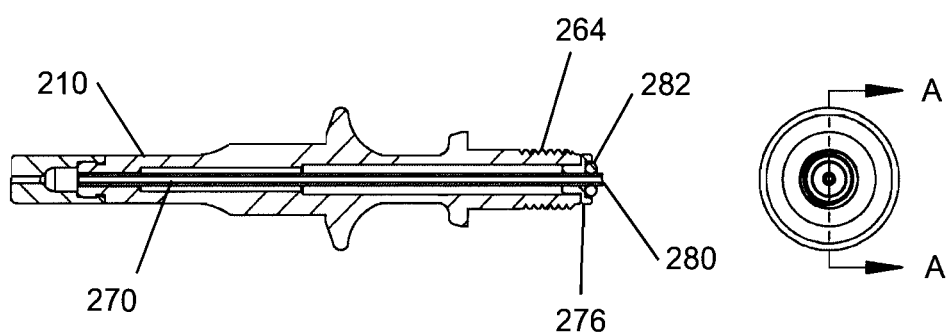
FIG. 30 is a front view of the dispensing member shown in FIG. 29.
FIG. 31 is a cross sectional view taken along lines A-A of FIG. 30.
Figure 32:
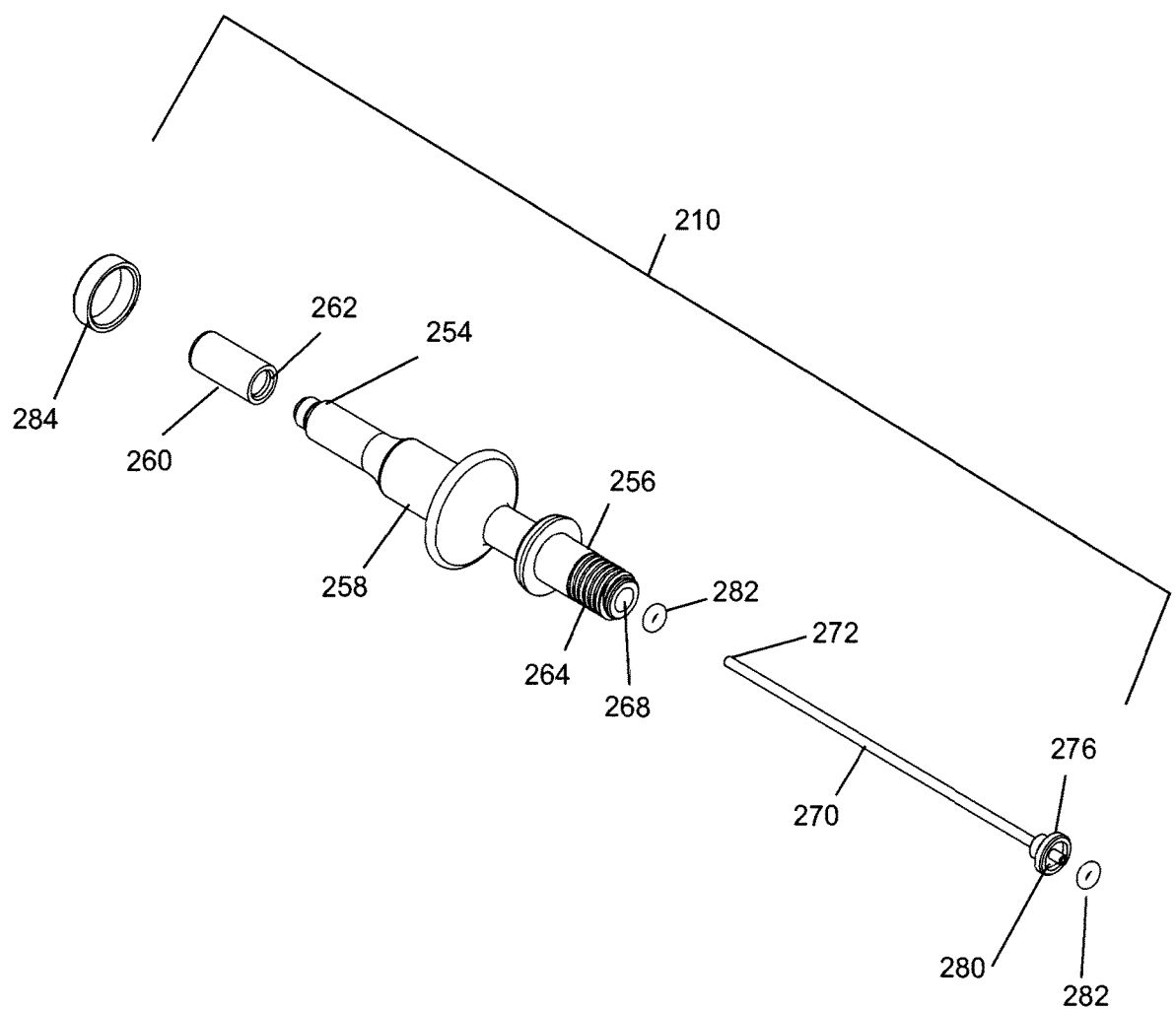
FIG. 32 is an exploded view of the dispensing member shown in FIG. 29.
Figure 33:
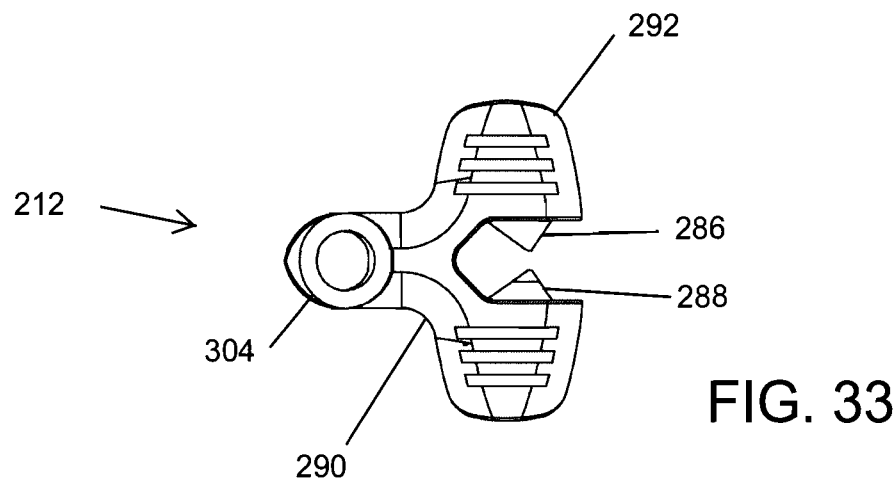
FIG. 33 is a plane view of an illustrative example of the syringe barrel securing device, showing a front side.
Figure 34:
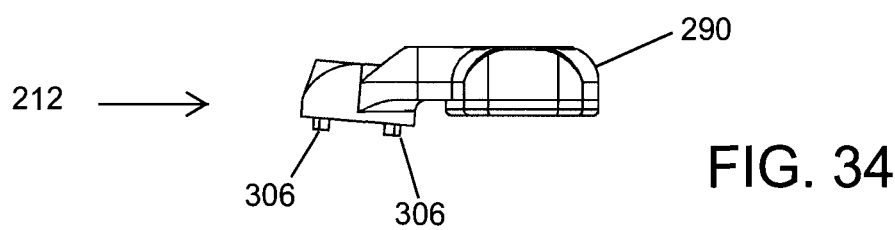
FIG. 34 is a side view of the syringe barrel securing device shown in FIG. 33.
Figure 35:
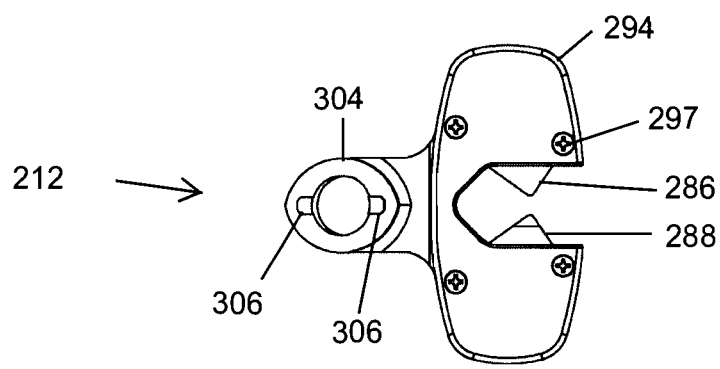
FIG. 35 is a plane view of an illustrative example of the syringe barrel securing device, showing a back side.

Referring to FIGS. 26 and 27, an illustrative example of the module chamber frame 218 is shown with the dispensing member 210, the syringe barrel securing device 212, the dispensing trigger 214, and the canister lift lever 216 removed. The module chamber frame 218 is shown assuming a generally tubular shape. However, such shape is illustrative only. FIG. 26 illustrates the back end 220, i.e. the end furthest away from a patient's skin, receiving the gaseous (vapor) anesthetizing composition. Running the length of the back end 220, from the upper portion 222 of the module chamber frame 218 to the lower portion 224 is a channel 226. The channel 226 is sized and shaped to receive and hold at least a portion of the canister lift lever 216. A canister lift stop, illustrated herein as a canister lift stop elongated body or wall 227 prevents the at least one portion of the canister lift from being moved or pushed into the center of the module chamber frame 218. The channel 226 terminates at the bottom end in an opening. The opening 228 is sized and shaped to receive a canister 11 when inserted therein and remain within the interior portion 232 (FIG. 28) of the module chamber frame 218. The opening 228 is shown having an elongated shape defined by curved surfaces 234 and 236, thus forming a module chamber frame tail end 238 that ends below the end of the channel 226.

FIG. 27 illustrates the front end 240, i.e. the end closest to the patient's skin receiving the gaseous (vapor) anesthetizing composition, of the module chamber frame 218. At or near the upper portion 222 is a dispensing member receiving area 242, illustrated herein as an opening 244 with an internal passageway 246 that terminates in an end wall 248. An outer module chamber frame fluid dispensing opening 250 positioned in the end wall 248 allows for fluid contained in canister 11 to dispense into the dispensing member 210 when secured to the dispensing member receiving area 242 and activated by triggering or pressing down on dispensing trigger 214. When canister 11 is inserted into the interior portion 232 (FIG. 28) of the module chamber frame 218, the dispensing tube 58 of the canister 11 (see FIG. 22) is pressed against the dispenser tube shoulder 55 to cause the canister valve 17 to open, allowing compressed gas to escape through the dispenser tube 58. Since the dispensing tube 58 is aligned with and inserted into the inner module chamber frame fluid dispensing opening 252, the compressed gas is directed to the dispensing member 210 via the inner module chamber frame fluid dispensing opening 252 and through the outer module chamber frame fluid dispensing opening 250.

The dispensing member 210 is designed to deliver a treatment fluid, i.e. pressurized gaseous (vapor) anesthetizing composition to a patient's skin. The dispensing member 210 may comprise a first fluid dispensing end 254, a second, opposing module connecting end 256, and a dispensing member main body 258, which may also be referred to as a nozzle, therebetween.

The dispensing member 210 is sized, shaped, or orientated to direct said gaseous anesthetizing composition to intersect with a delivery axis 30 (see FIG. 2) of a needle connected to said module 202. The first fluid dispensing end 254 is shown having a cap 260 attached thereto via threading 262. The second, opposing module connecting end 256, via threading, connects or secures to the module 202 at threading 266 (see FIG. 27) within the dispensing member receiving area 242. The dispensing member main body 258 has an inner lumen 268 sized and shaped to receive and hold therein an inner fluid dispensing tube 270. The inner fluid dispensing tube 270 is preferably sized to traverse the length of the dispensing member main body 258 and has an opening at a first end 272. The second end may contain a shoulder 276, with a portion of the dispensing tube 270 extending through. The extended portion 280 is in contact with the opening 250 when the dispensing member 210 is connected to the module 202. Washers 282 help create a tight seal and prevent fluid escape. An indicator ring 284, which may be colored, may be used to help the user identify the size of the dispensing member 210, i.e. a red ring to indicate a short dispensing member 210, a white ring to indicate a medium dispensing member 210, or a blue ring to indicate a long dispensing member 210.

Figure 36:
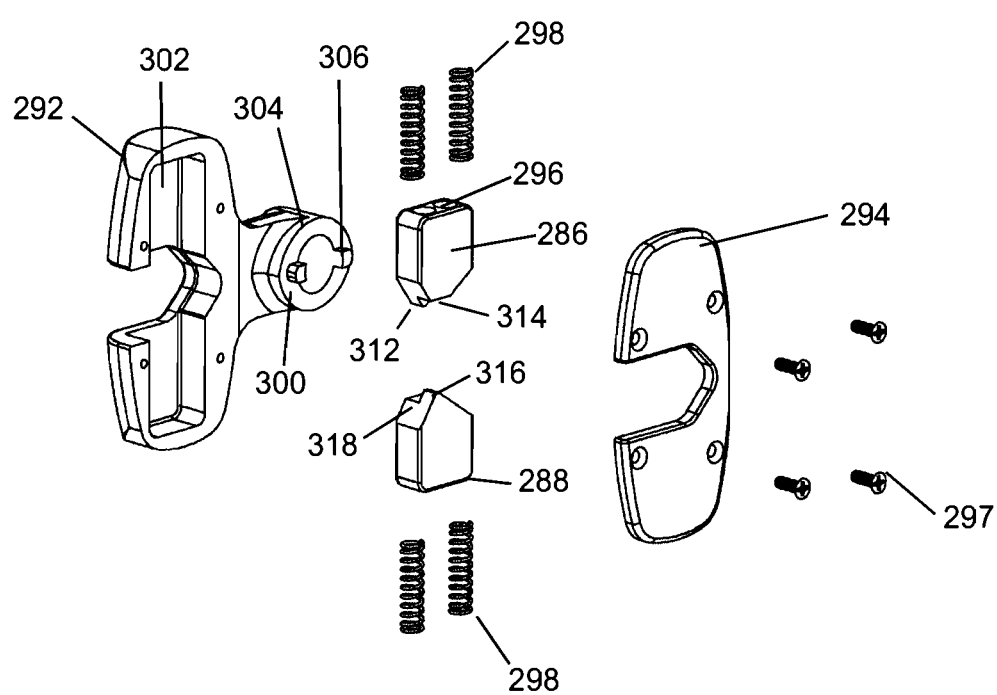
FIG. 36 is an exploded view of the syringe barrel securing device shown in FIG. 33.

At least a portion of the dispensing member 210 may be used to support the syringe barrel securing device 212. The syringe barrel securing device 212 is designed to securely hold a syringe, particularly at the orientation and distance so as not to interfere with the dispensing of the pressurized gaseous (vapor) anesthetizing composition from the dispensing member 210. The syringe barrel securing device 212 contains two spring loaded clamping bodies 286 and 288 placed within the barrel securing device housing structure 290. The securing device housing structure 290 comprises an upper portion 292 secured to a lower portion 294 via screws 297. The clamping bodies 286 and 288 each have openings 296 (see FIG. 36, shown for clamp body 286 only) which secure the springs 298. The clamping bodies 286 and 288 are sized and shaped to fit and move, by sliding linearly, within the cut-out portion or channels 300 and 302 in the upper portion 292. The syringe barrel securing device 212 attaches to the dispensing member 210 via a securing member in the form of a generally circular shaped sleeve 304. The sleeve 304 secures to the module chamber frame 218 via shaped prongs, tabs or appendages 306. The shaped prongs, tabs, or appendages 306 are sized and shaped to engage and fit within the slotted recesses 308 and 310 (FIG. 27) formed within the dispensing member receiving area 242. The shaped prongs or appendages 306 may also act as orientation tabs to insure a preferred orientation between said syringe barrel securing device and said least one portion of said modular chamber frame. The clamping body 286 may be configured so that the end which interacts with an inserted syringe has terminal end, shown as a pointed terminal end 312 that rises above a generally planar surface 314. The clamping body 288 may be configured to have a terminal end which interacts with an inserted syringe, shown as pointed terminal end 316 that rises above a generally planar surface 318, see FIGS. 24 and 36. The terminal ends 312 and 316 are arranged in a opposite orientation relative to each other so that when there is no body acting upon the clamps 286 and 288, the pointed terminal end 312 of clamp 286 rests against the planar surface 318 of clamp 288 and the pointed terminal end 316 of clamp 288 rests on the generally planar surface 314 of clamp 286.

Figures 37, 38:
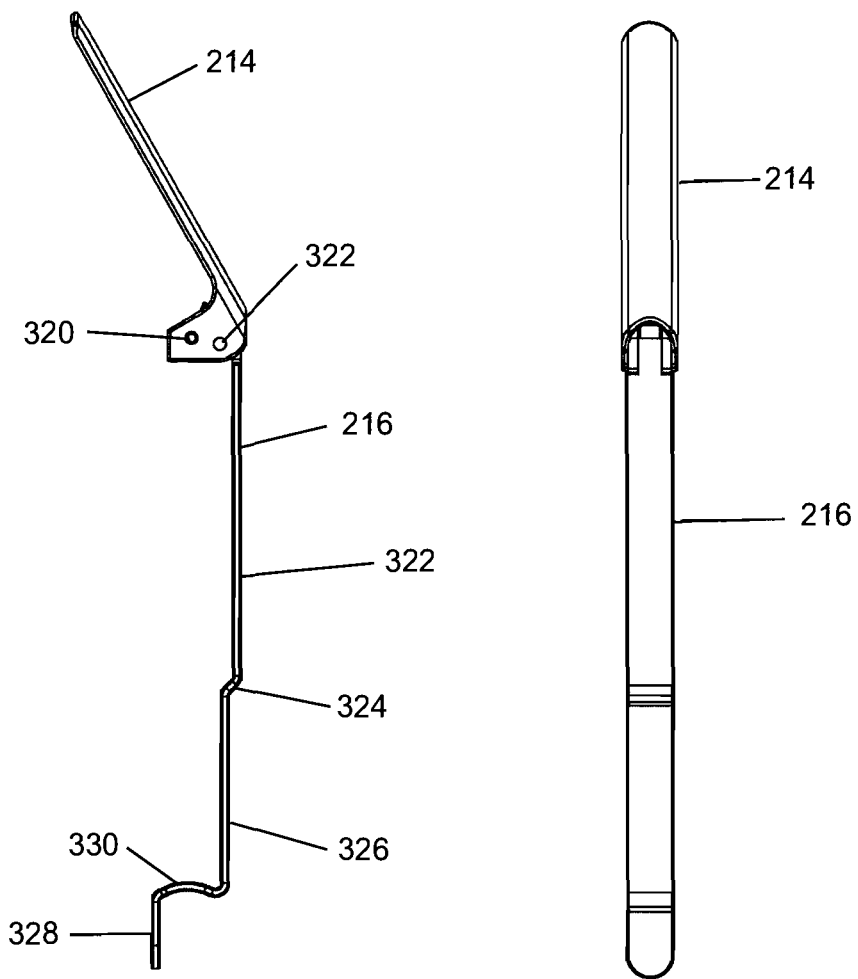
FIG. 37 is a perspective view of the dispensing trigger and canister lift lever.
FIG. 38 is a plan view of the dispensing trigger and canister lift lever.
Figure 39:
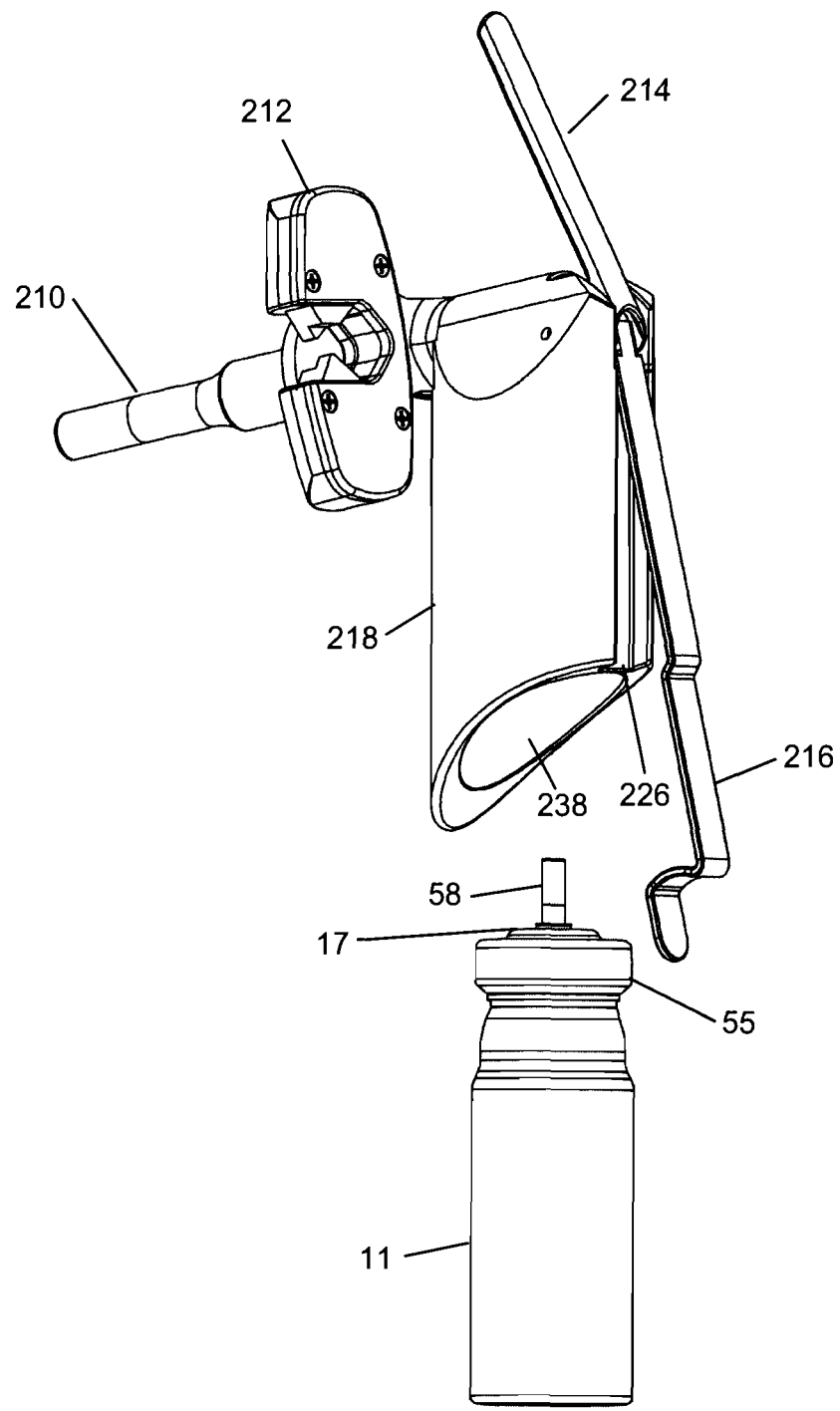
FIG. 39 illustrates the applicator for dispensing a fluid shown prior to insertion of a canister.
Figure 40:
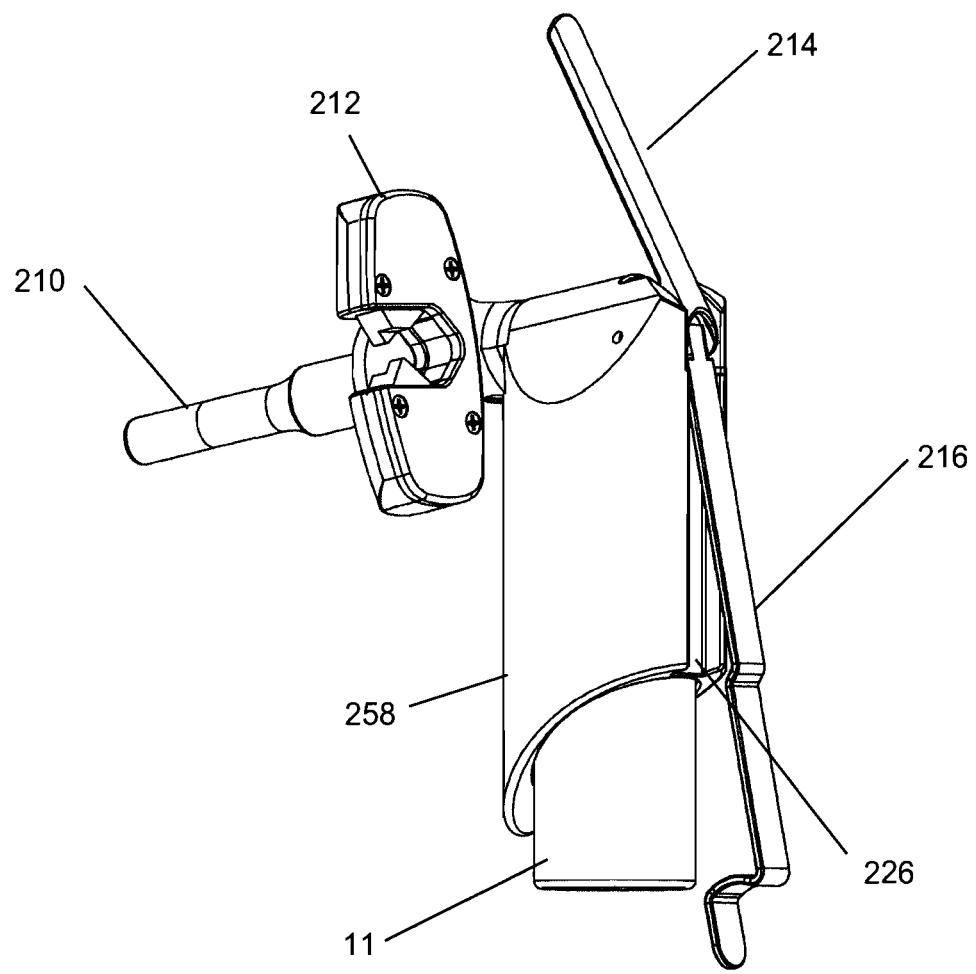
FIG. 40 illustrates the applicator for dispensing a fluid shown with insertion of a canister.
Figure 41:
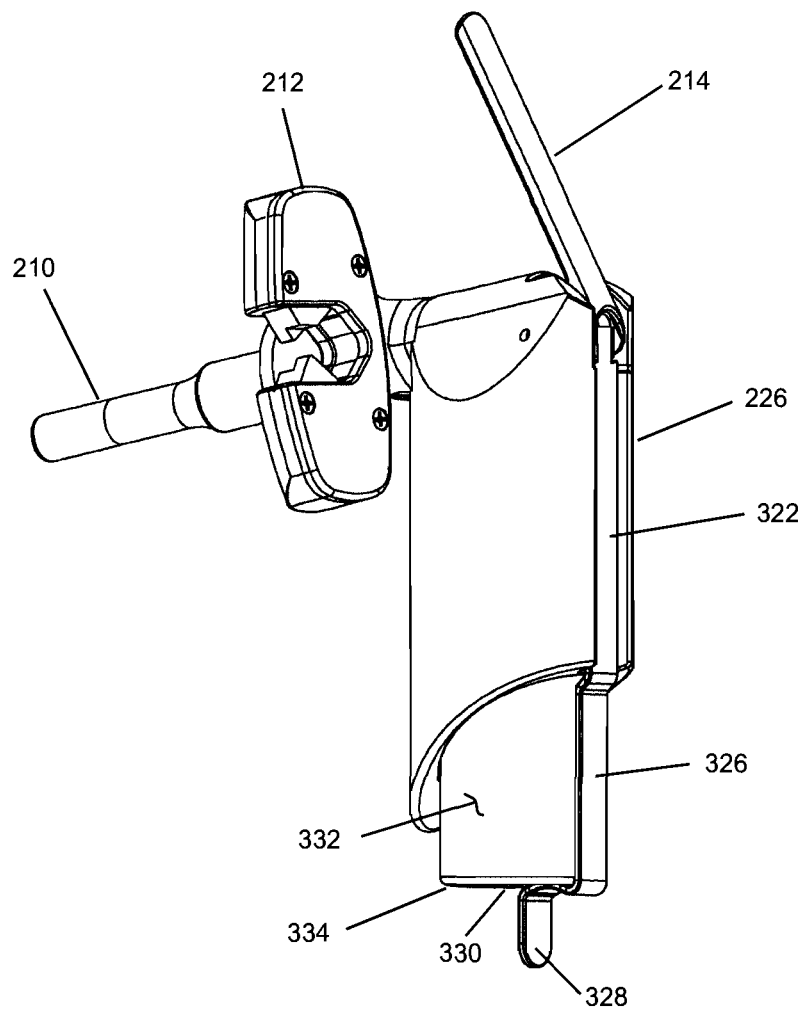
FIG. 41 illustrates the applicator for dispensing a fluid shown with the canister secured thereto.

FIGS. 37 and 38 illustrate the dispensing trigger 214 secured to the canister lift lever 216, (which connect to the dispensing member main body 258, not shown in the figures), through pins 320 and 322. The canister lift lever 216 may comprise a first elongated portion 322 sized and shaped to fit within the channel 226, a second curved or concave portion 324, and a second elongated portion 326, extending downwardly from the curved or concave portion 324. The second elongated portion 326 is positioned inwardly relative to the first elongated portion 322. The second elongated portion 326 ends in a hooked end portion 328. The hooked end portion 328 forms a seat 330 which can secure against a bottom surface of the canister 11 to secure it in place. Since the dispensing trigger 214 is secured to the canister lift lever 216, pressing the dispensing trigger causes the canister lift lever 216 to push the canister in an upward movement, thus providing a mechanism to deliver a metered amount of the gaseous (vaporous) anesthetizing composition. FIGS. 39-41 illustrate the steps of securing the canister 11 to the module chamber frame 218. In FIG. 39, the canister 11 is show prior to insertion into opening 228 of the module chamber frame 218. FIG. 40 illustrates the canister 11 inserted into the module chamber frame 218. FIG. 41 illustrates the canister 11 secured within the module chamber frame 218 via securing of the canister lift lever 216 to the canister 11. In this position, the first elongated portion 322 rests within channel 226. The second elongated portion 326 rests against a portion of the canister 11 outer surface 332 and the seat 330 of the hooked end portion 328 rests against and secures the bottom surface 334 of canister 11.

Figure 42:
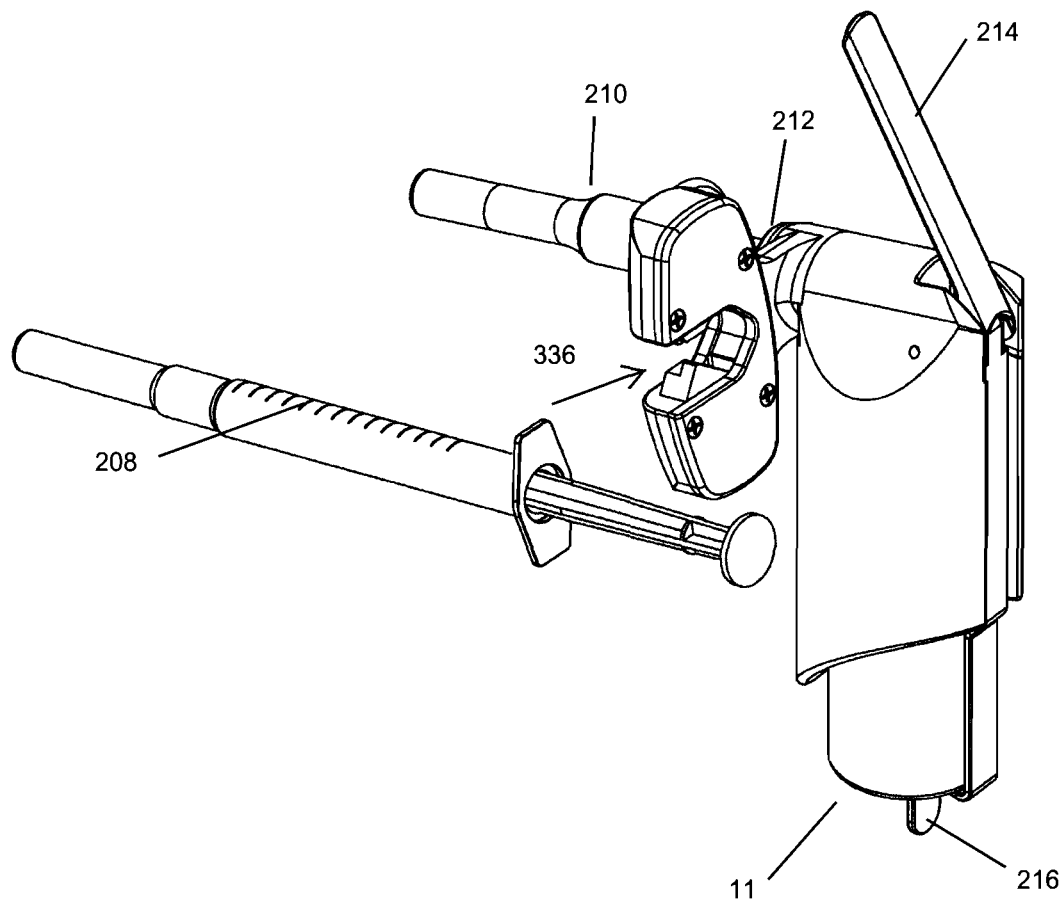
FIG. 42 illustrates the applicator for dispensing a fluid shown prior to securing a syringe thereto.
Figure 43:
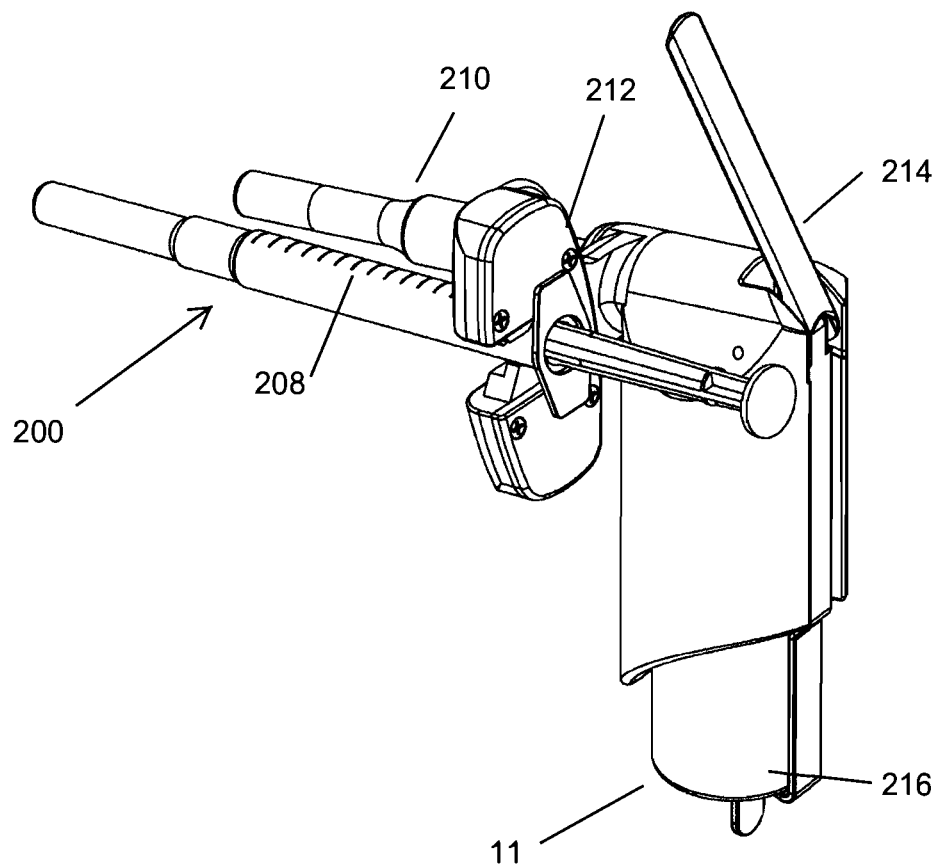
FIG. 43 illustrates the applicator for dispensing a fluid, shown prior to securing the syringe thereto.

FIGS. 42 and 43 illustrate the attachment of a syringe to the applicator 200. As shown, the canister 11 is inserted into the module chamber frame 218 and secured with the canister lift lever 216 locked in place. Syringe barrel 208 of syringe 204 is secured to the applicator 200 by placing the syringe barrel 208 into the syringe barrel securing device 212, see arrow 336. The syringe barrel 208 of syringe 204 secures between clamps 286 and 288 as the force exerted causes the spring-loaded clamps 286 and 288 to move or open up from their original resting state. In this position, the user can dispense metered amounts of the gaseous (vaporous) anesthetizing composition by pressing on the dispensing trigger 214. Such action causes the canister lift lever 216 to move upwardly, i.e. towards the inserted syringe barrel 208 of syringe 204, causing the gaseous (vaporous) anesthetizing composition to be dispensed from the canister 11, out from the dispensing member 210, and delivered to the patient's skin. The user can then dispense the contents of the syringe 204 to the skin thereafter.

Figure 44:
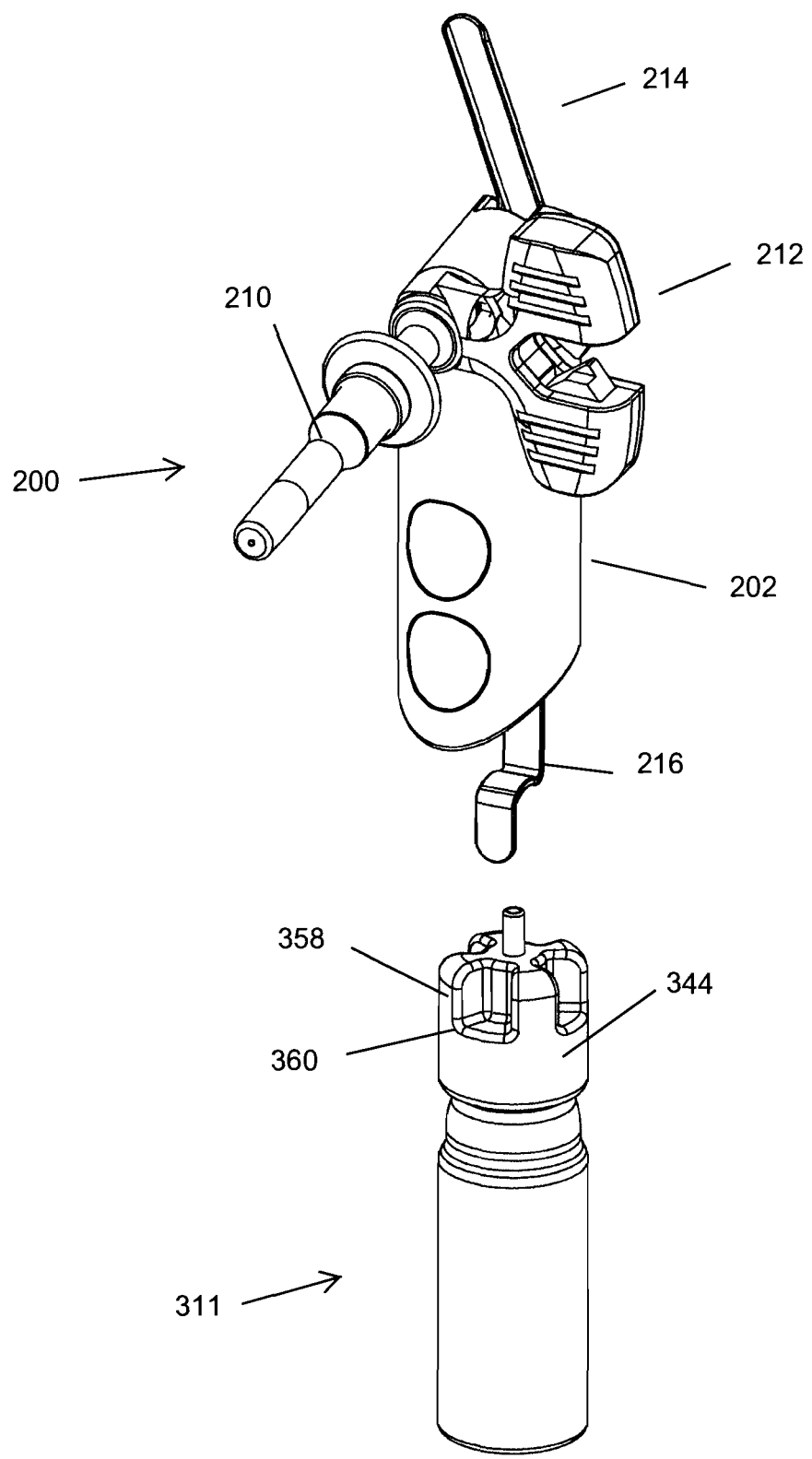
FIG. 44 is a perspective view of the applicator for dispensing a fluid with a modified canister.
Figure 45:
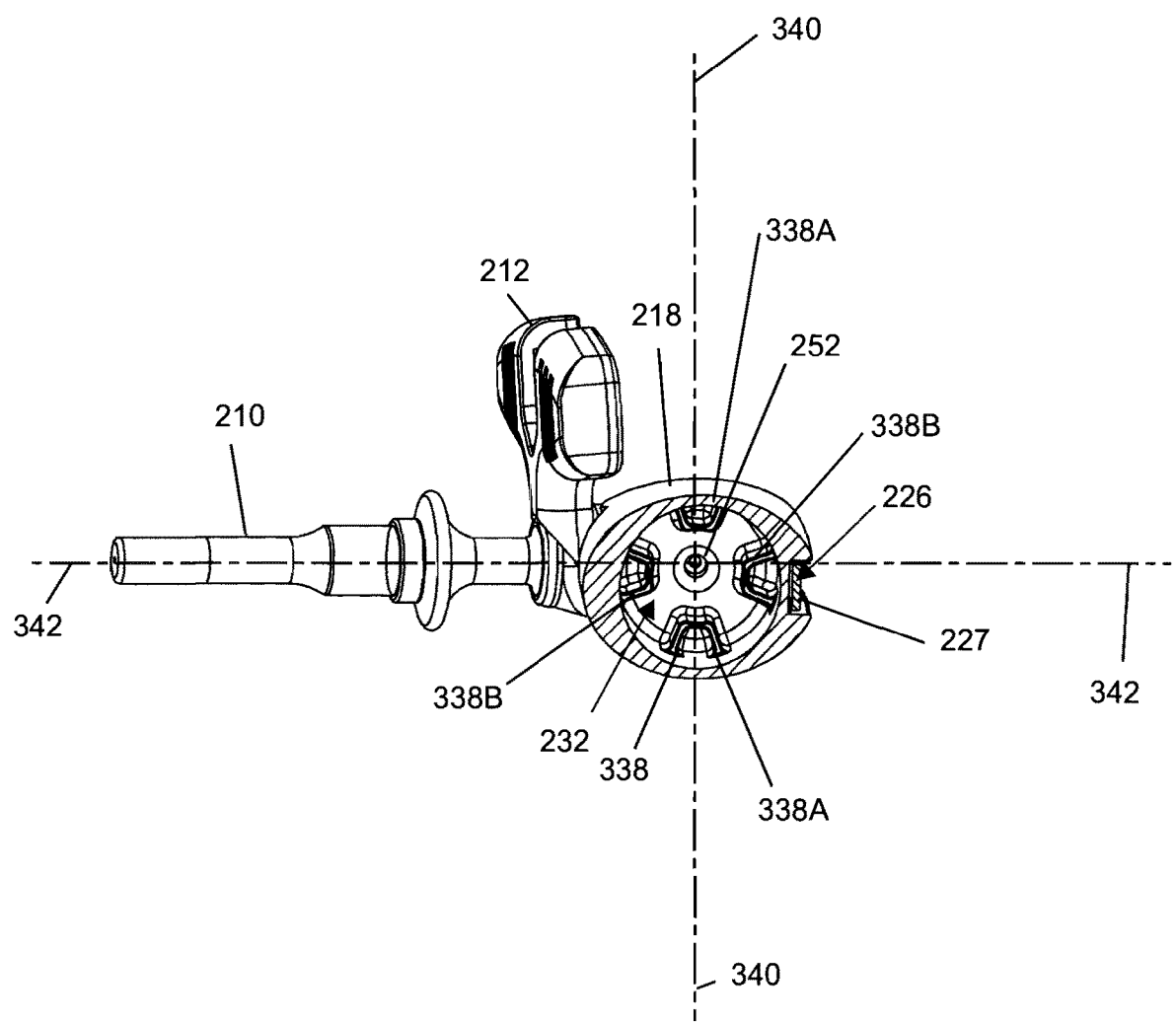
FIG. 45 is a bottom view of the applicator for dispensing a fluid illustrated in FIG. 44, with the modified canister removed.

Referring to FIG. 44, the embodiment of the applicator 200 illustrated is configured to secure and engage a modified canister 311. The applicator 200 shown may include all or some of the features as previously described, with several additional components to be used to engage and secure the modified canister 311. Positioned within the interior portion 232 of the module chamber frame 218 are one or more ribs 338, see FIG. 45. The one or more ribs 338 may be integrally formed or separately attached and secured to the inner wall 340 of the module chamber frame 218, and extend outwardly from the inner wall 340 towards the center. FIG. 45 illustrates four ribs 338, a first pair 338A, arranged oppositely about opening 252 and arranged in the same first plane (see dashed lines 340), and a second pair, 338B, arranged oppositely about opening 252 and arranged in the same second plane (see dashed line 342), with the second plane 342 being different than the first plane 340. The ribs 338 are sized, shaped, and spaced apart to engage with a modified canister cap 344.

Figure 46:
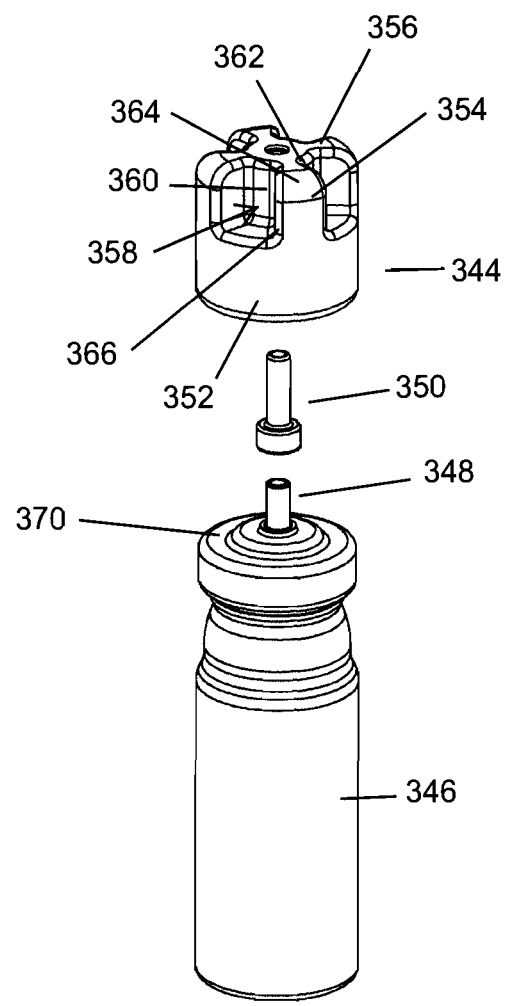
FIG. 46 is an exploded view of the modified canister.
Figure 47:
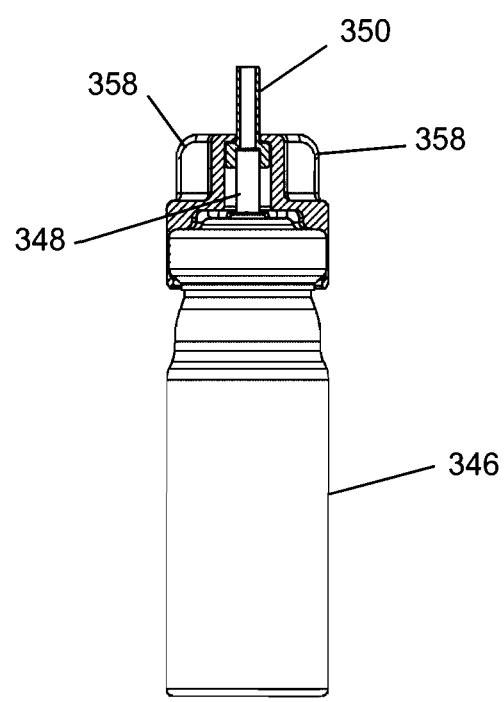
FIG. 47 is a partial cross sectional view of the modified canister.
Figure 48:
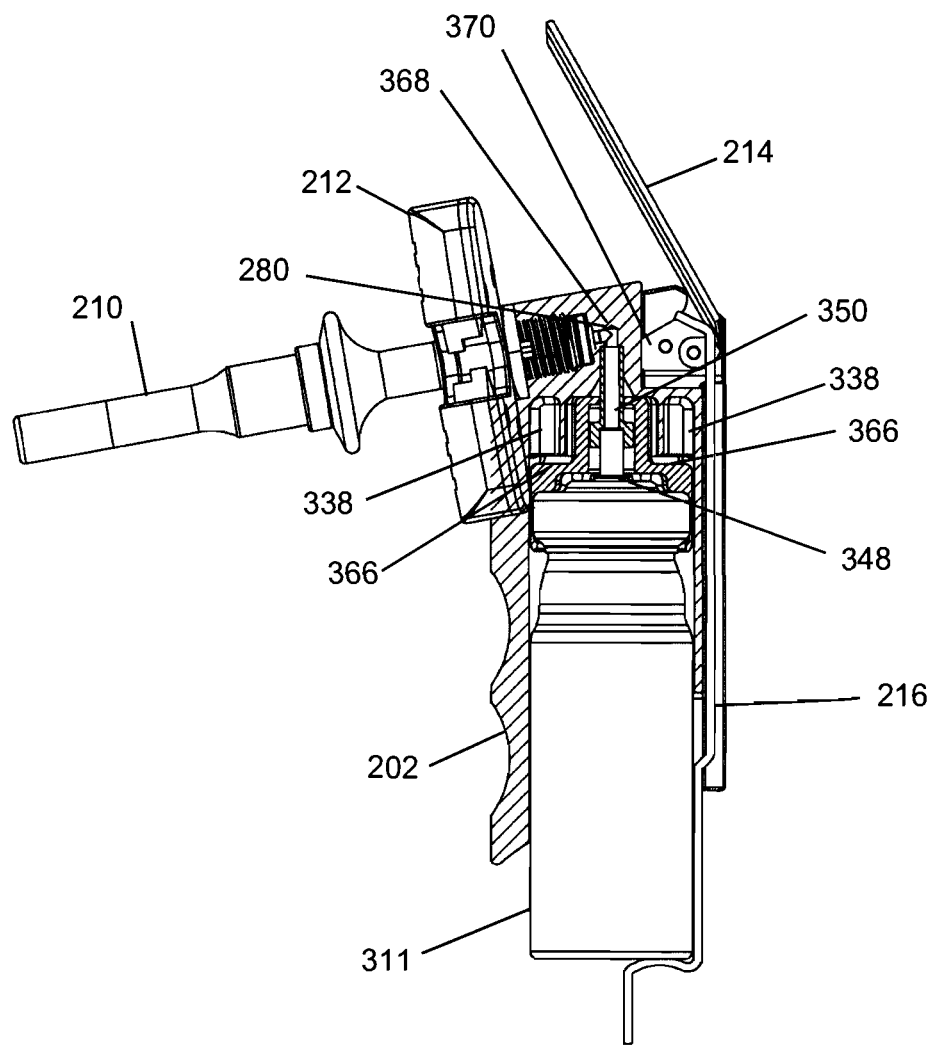
FIG. 48 is a partial cross-sectional view of the applicator, with the modified canister inserted therein.
Figure 49:
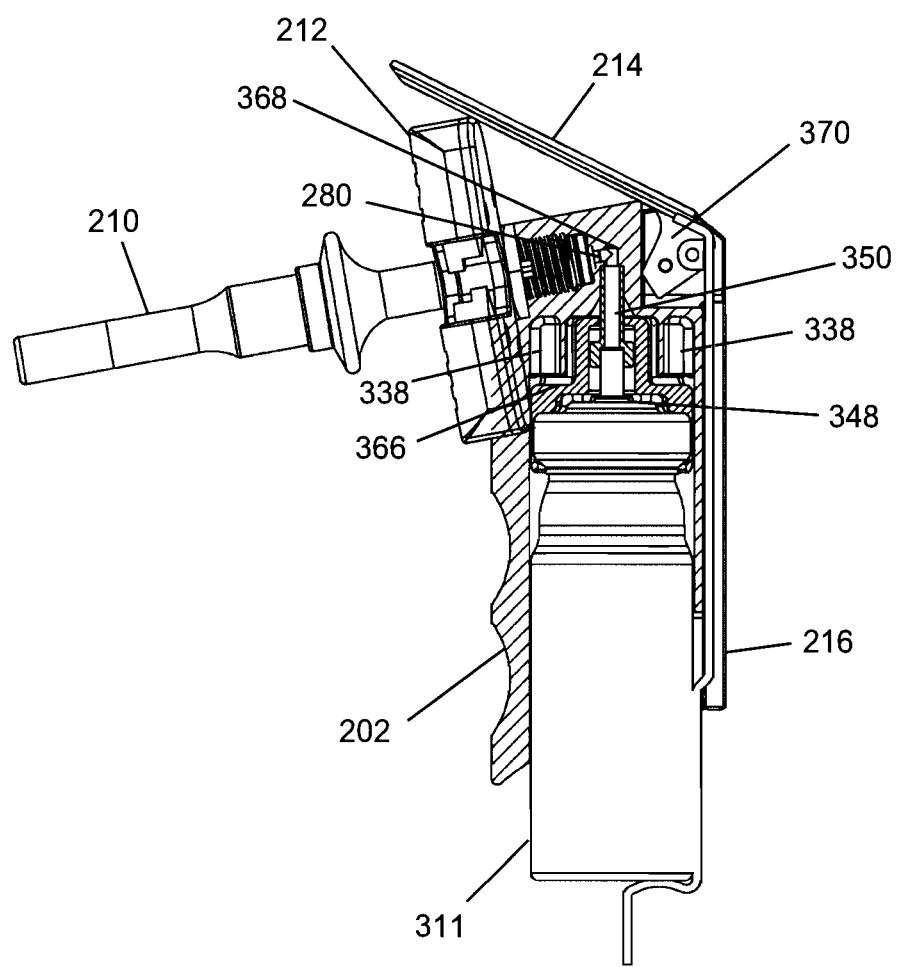
FIG. 49 is a second partial cross-sectional view of the applicator, with the modified canister inserted therein.
Figure 50:
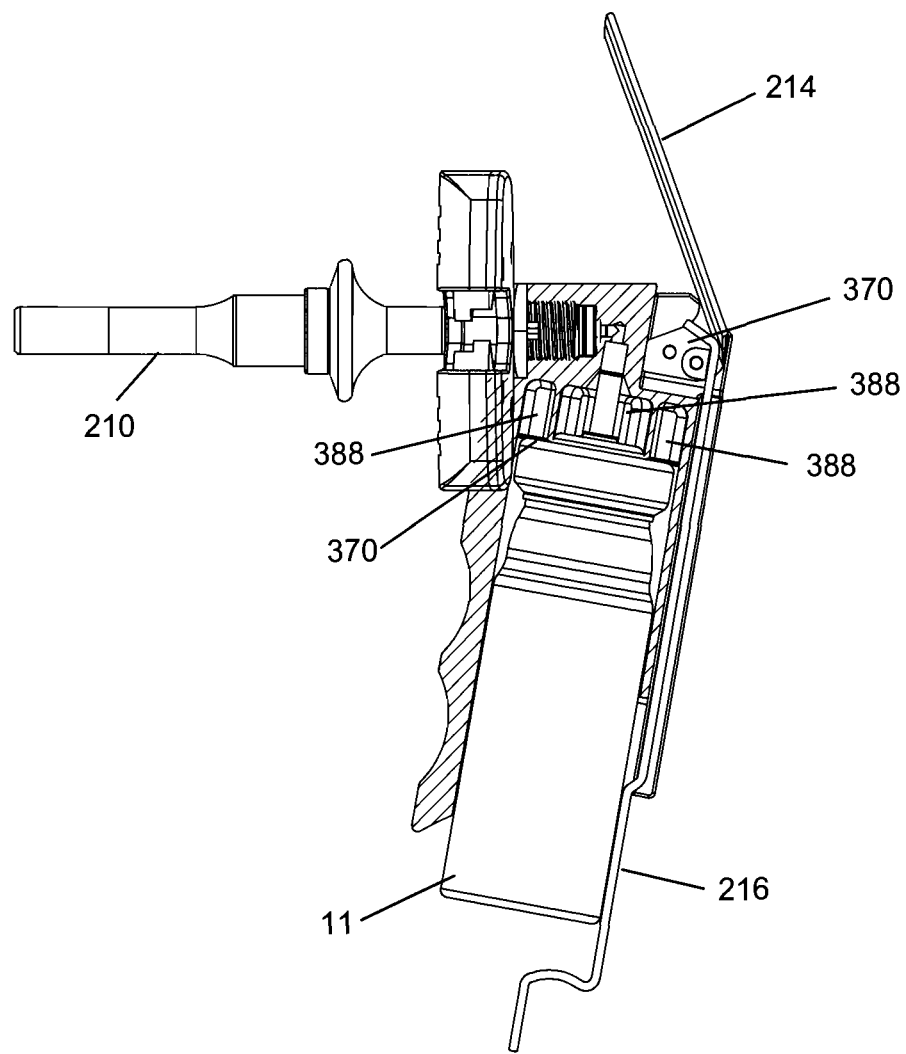
FIG. 50 is a partial cross-sectional view of the applicator, with a canister inserted therein.

Referring to FIG. 46, the modified canister 311 is shown having a main body 346, which is sized and shaped to store the gaseous (vaporous) anesthetizing composition therein, a metering valve 348, and a valve stem 350. The modified canister cap 344 may comprise an open bottom end 352 to allow securing to a portion of the main body 346, and a top end 354 having an opening 356 sized and shaped to allow passage of the valve stem 350 therethrough. The modified canister cap 344 comprises a plurality of applicator receiving members 358, illustrated herein as shaped openings. The applicator receiving members 358 are sized and shaped to correspond to fit with and engage ribs 338 so that the applicator receiving members 358 and the ribs 338 engage, they are locked or remain in place, preferably by a frictional fit. A sufficient force can be applied to pull off or disengage the ribs 338-applicator receiving members 358 bond. Each applicator receiving member 358 may be defined by two generally parallel arranged side walls 360, 362, a back wall 364, and a bottom wall or seat 366, each shaped to provide a secure fit with the ribs 338. Once the modified canister 311 is inserted into the applicator 200, see FIGS. 48 and 49, and secured by manipulation of the canister lift lever 216, the canister is secured by engagement of the ribs 338 with the applicator receiving members 358, thus aligning a metering valve 348 and a valve stem 350 in position to disperse the gaseous (vaporous) anesthetizing composition into the spray orifice 368 and through the dispensing member 210. A pivoting block member 370 may be used to maintain the modified canister 311 (or canister 11) in place. Referring to FIG. 50, the applicator 200 having ribs 338 is shown engaging with a canister 11 that does not include the modified canister cap 344. In this case, the ribs 338 rest against a shoulder 370 of the canister 11.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A dental applicator for dispensing one or more compositions comprising:
   a module configured to be removably attached to a syringe and which accommodates a canister having a pressurized gaseous anesthetizing composition,
   a dispensing member having an elongated outlet nozzle for directing and agent dispensed therefrom to intersect with a delivery axis of a needle connected to said syringe when said syringe is attached to said module,
   a dispensing trigger;
   a canister lift lever; and
   syringe barrel securing device configured to secure and hold said syringe when said syringe is attached thereto.

2. The dental applicator for dispensing one or more compositions according to claim 1 wherein said module includes a modular chamber frame having an interior region sized and shaped for slidably receiving and securing said canister within, said canister including a dispensing tube in mechanical cooperation with at least one portion of said modular chamber frame so that sliding said canister within said adjunct chamber frame causes said gaseous anesthetizing composition to be directed from said canister through said outlet nozzle.

3. The dental applicator for dispensing one or more compositions according to claim 2 wherein said syringe barrel securing device configured to secure and hold said syringe when said syringe is attached thereto comprises at least two members configured for securing said syringe barrel in place.

4. The dental applicator for dispensing one or more compositions according to claim 3 wherein said at least two members configured for securing said syringe barrel in place include two opposing spring loaded clamping members.

5. The dental applicator for dispensing one or more compositions according to claim 4 wherein said syringe barrel securing device incudes an housing having an first upper portion and a lower second portion.

6. The dental applicator for dispensing one or more compositions according to claim 5 wherein said first upper portion comprises channels or slots sized and shaped to hold and allow said two opposing spring loaded clamping members to move therein.

7. The dental applicator for dispensing one or more compositions according to claim 5 syringe barrel securing device incudes a securing sleeve configured to attach to said at least one portion of said modular chamber frame.

8. The dental applicator for dispensing one or more compositions according to claim 7 wherein said syringe barrel securing device securing sleeve comprises one or more securing and orientation tabs to insure a preferred orientation between said syringe barrel securing device and said least one portion of said modular chamber frame.

9. The dental applicator for dispensing one or more compositions according to claim 3 wherein said dispensing trigger and said canister lift lever are secured together to said module by one or more pins.

10. The dental applicator for dispensing one or more compositions according to claim 3 wherein said canister lift lever is sized to run at least an entire length of said modular chamber frame.

11. The dental applicator for dispensing one or more compositions according to claim 10 wherein at least a portion of said canister lift lever is longer than an entire length of said modular chamber frame.

12. The dental applicator for dispensing one or more compositions according to claim 3 wherein at least a portion of said canister lift lever is configured to engage with said canister when said canister is inserted within said modular chamber frame.

13. The dental applicator for dispensing one or more compositions according to claim 12 wherein said canister lift lever is configured to align said canister secured thereto in an orientation wherein said modular chamber frame cooperates with a valve assembly of said canister to cause the pressurized gaseous anesthetizing composition to be dispensed.

14. The dental applicator for dispensing one or more compositions according to claim 2 wherein said modular chamber frame comprises one or more internal ribs configured to engage with said canister when said canister is inserted therein.

15. The dental applicator for dispensing one or more compositions according to claim 1 wherein said outlet nozzle is tubular in construction having a distal end with an opening, and a passageway to cause said anesthetic sprayed therefrom to spray in a desired pattern.

16. The dental applicator for dispensing one or more compositions according to claim 1 wherein said agent is pressurized gaseous anesthetizing composition.

17. The dental applicator for dispensing one or more compositions according to claim 16 wherein said agent is pressurized gaseous anesthetizing composition is an aerosol propellant that decreases the temperature of a user's skin to cause numbness.

18. The dental applicator for dispensing one or more compositions according to claim 16 wherein said endothermic gas anesthetic is a mixture of more than one aerosol propellants that decreases the temperature of a user's skin to cause numbness.

19. The dental applicator for dispensing one or more compositions according to claim 16 wherein said pressurized gaseous anesthetizing composition is an aerosol propellant that decreases the temperature of a user's skin to cause numbness, said endothermic gas anesthetic including an anti-bacterial.

20. The dental applicator for dispensing one or more compositions according to claim 1 wherein said canister is a metal canister having a valve assembly crimped and sealed within an open end of said canister to create a sealed pressure canister, said valve assembly including a dispenser tube extending outwardly therefrom.

21. The dental applicator for dispensing one or more compositions according to claim 1 further including a syringe secured to said syringe barrel securing device.

22. A method of using a dental applicator with an attached endothermic gas anesthetic assembly comprising the steps of:
   placing the dental applicator according to claim 1 against the injection site, said dental applicator comprising a mendicant filled syringe secured to said syringe barrel securing device;
   locking said a canister lift lever to a canister having endothermic gas anesthetic inserted therein;
   pressing said a dispensing trigger causing said endothermic gas anesthetic to be dispersed or sprayed to a surface area of a patient where an injection is to take place.

23. The method of using a dental applicator with an attached endothermic gas anesthetic assembly according to claim 22 further including the step of penetrate g the skin of said patient with a needle attached to said syringe and injecting said medicant from said syringe.

* * * * *